(12) United States Patent
Stinchcomb et al.

(10) Patent No.: US 9,533,942 B2
(45) Date of Patent: Jan. 3, 2017

(54) USE OF CANNABIDIOL PRODRUGS IN TOPICAL AND TRANSDERMAL ADMINISTRATION WITH MICRONEEDLES

(71) Applicant: ZYNERBA PHARMACEUTICALS, INC., New York, NY (US)

(72) Inventors: Audra Lynn Stinchcomb, Lexington, KY (US); Stan Lee Banks, Frankfort, KY (US); Miroslaw Jerzy Golinski, Lexington, KY (US); Jeffery Lynn Howard, Richmond, KY (US); Dana Carmel Hammell, Georgetown, KY (US)

(73) Assignee: Zynerba Pharmaceuticals, Inc., Devon, PA (US)

( * ) Notice: Subject to any disclaimer, the term of this patent is extended or adjusted under 35 U.S.C. 154(b) by 0 days.

(21) Appl. No.: 14/539,824

(22) Filed: Nov. 12, 2014

(65) Prior Publication Data
US 2015/0197484 A1    Jul. 16, 2015

Related U.S. Application Data

(63) Continuation of application No. 12/873,248, filed on Aug. 31, 2010, now abandoned.
(Continued)

(51) Int. Cl.
*A61K 9/00* (2006.01)
*C07C 229/12* (2006.01)
(Continued)

(52) U.S. Cl.
CPC .......... *C07C 229/12* (2013.01); *A61K 9/0014* (2013.01); *A61K 9/0021* (2013.01); *A61K 31/222* (2013.01); *A61K 31/225* (2013.01); *A61K 31/265* (2013.01); *A61K 31/27* (2013.01); *A61K 45/06* (2013.01); *C07C 219/04* (2013.01); *C07C 219/16* (2013.01); *C07C 229/16* (2013.01); *C07C 271/52* (2013.01); *A61K 9/7007* (2013.01); *C07C 2101/16* (2013.01)

(58) Field of Classification Search
CPC ....................................................... A61K 9/21
See application file for complete search history.

(56) References Cited

U.S. PATENT DOCUMENTS

| 6,566,560 B2 | 5/2003 | Travis |
| 2002/0111377 A1 | 8/2002 | Stinchcomb |

(Continued)

OTHER PUBLICATIONS

Communication pursuant to Article 94(3) EPC issued in European Application No. 10 755 265.5 dated May 18, 2015.
(Continued)

*Primary Examiner* — Benjamin Packard
(74) *Attorney, Agent, or Firm* — McCarter & English, LLP; Danielle L. Herritt

(57) ABSTRACT

Described herein are microneedle drug delivery systems comprising a pharmaceutical compositions comprising pharmaceutically active agents (e.g., cannabidiol and prodrugs of cannabidiol) and microneedle arrays suitable for local and systemic delivery of the active agent to a mammal. Also described herein are methods of using a microneedle transdermal or topical drug delivery systems comprising pharmaceutical compositions, comprising cannabidiol and prodrugs of cannabidiol, and microneedle arrays in the treatment disease, including pancreatitis and pancreatic cancer.

16 Claims, 1 Drawing Sheet

Related U.S. Application Data

(60) Provisional application No. 61/238,524, filed on Aug. 31, 2009.

(51) Int. Cl.
| | | |
|---|---|---|
| *C07C 219/16* | (2006.01) | |
| *C07C 229/16* | (2006.01) | |
| *C07C 271/52* | (2006.01) | |
| *A61K 31/222* | (2006.01) | |
| *A61K 31/225* | (2006.01) | |
| *A61K 31/265* | (2006.01) | |
| *A61K 31/27* | (2006.01) | |
| *A61K 45/06* | (2006.01) | |
| *C07C 219/04* | (2006.01) | |
| *A61K 9/70* | (2006.01) | |

(56) References Cited

U.S. PATENT DOCUMENTS

| | | |
|---|---|---|
| 2006/0084695 A1 | 4/2006 | Griffin et al. |
| 2006/0216251 A1 | 9/2006 | Morariu |
| 2009/0036523 A1 | 2/2009 | Stinchcomb et al. |

OTHER PUBLICATIONS

Final Office Action issued in U.S. Appl. No. 12/873,248 dated Dec. 12, 2013.
Non-Final Office Action issued in U.S. Appl. No. 12/873,248 dated Mar. 20, 2013.

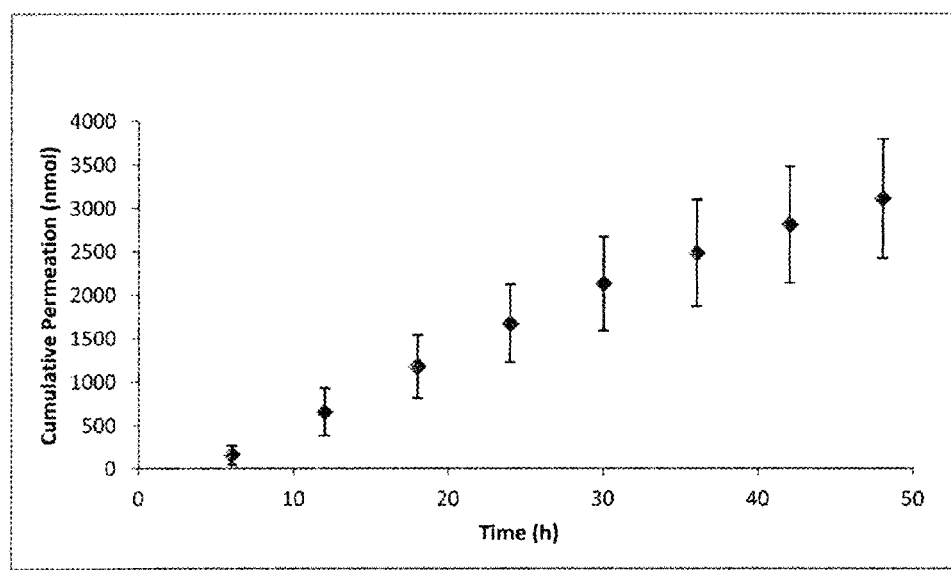

USE OF CANNABIDIOL PRODRUGS IN TOPICAL AND TRANSDERMAL ADMINISTRATION WITH MICRONEEDLES

CROSS-REFERENCE TO RELATED APPLICATIONS

This application claims the benefit of U.S. Provisional Application No. 61/238,524, filed on Aug. 31, 2009, which is hereby incorporated by reference in its entirety to the extent permitted by law.

FIELD

Described herein are microneedle drug delivery systems comprising: a pharmaceutical composition comprising pharmaceutically active agents (e.g., cannabinoids, such as cannabidiol or prodrugs of cannabidiol) and microneedle arrays suitable for local and systemic delivery to a mammal, including systemic transdermal delivery and topical delivery. Also described herein are methods of using a microneedle transdermal or topical drug delivery system comprising a pharmaceutical composition, comprising a cannabinoid (such as cannabidiol or prodrugs of cannabidiol), and a microneedle array in the treatment of a disease responsive to cannabinoid therapy

BACKGROUND

It has now been found that a pharmaceutical composition comprising a cannabinoid, such as cannabidiol, or a cannabinoid prodrug, such as a cannabidiol prodrug, can be transdermally administered to a mammal in conjunction with a microneedle array to treat a medical condition responsive to cannabinoids, such as alcohol use disorders, pain, inflammation and pancreatic diseases, such as pancreatic cancer and pancreatitis, via transdermal or topical drug delivery systems. It has further been found that microneedle transdermal or topical drug delivery systems comprising a pharmaceutical composition, comprising a cannabinoid or cannabinoid prodrug and a penetration enhancer (i.e., co-solvent), and a microneedle array can be used to treat a medical condition responsive to cannabinoids, such as alcohol use disorders, pain, inflammation and pancreatic diseases, such as pancreatic cancer and pancreatitis. It has further been found that microneedle transdermal or topical drug delivery systems comprising a pharmaceutical composition, comprising a cannabinoid or cannabinoid prodrug, a microneedle array and a COX inhibitor, such that the duration in which the microneedle created pore will remain open is increased, can be administered to a mammal. Suitable COX inhibitors include diclofenac and ibuprofen.

The pharmaceutical compositions described herein are suitable for use with a COX inhibitor-containing gel or hydrogel which has been optionally incorporated into a patch. In one embodiment, the COX inhibitor-containing gel or hydrogel which has been optionally incorporated into a patch is distinct from the pharmaceutical composition containing a cannabinoid or a cannabinoid prodrug and is applied to the skin surface either before, during or after the skin has been treated with a microneedle array. In another embodiment, the pharmaceutical compositions comprising the cannabinoid or cannabinoid prodrug further comprises a COX-inhibitor and is administered as a gel or hydrogel which has been optionally incorporated into a patch that is applied to the skin surface either before, during or after the skin had been treated with a microneedle array.

Cannabinoids and Cannabidiol

Cannabinoids, including cannabidiol ("CBD"), have recently been found useful in treating pancreatic illnesses. For example, it has been found that cannabidiol is useful in the treatment of acute and chronic pancreatitis. Pancreatitis is widely known as a very painful disease and can ultimately lead to pancreatic cancer. It has been found that cannabidiol has anti-inflammatory activity that results in a decrease of pain in pancreatitis cases. Pancreatic cancer is the fourth most common fatal cancer in the United States and fifth most prevalent worldwide. Cannabinoids, such as tetrahydrocannabinol and the synthetic cannabinoid WIN 55,212-2, have been found to induce apoptosis of pancreatic tumor cells in vitro and in vivo. Cannabidiol has the same potential to cause the same cascade that results in tumor cell death and diminish proliferation to lateral tumor formation.

In addition, the clinical usefulness of cannabinoids, including cannabidiol, to provide analgesia and neuroprotection, reduce inflammation, help alleviate nausea and emesis, as well as treat epilepsy, anxiety disorders and glaucoma, has been well-recognized. In addition, it is also well-known that cannabidiol lacks the psychoactive effects seen in many of the other cannabinoids, including $\Delta^9$-tetrahydrocannabinol, which is currently available in an oral dosage form, sold under the trade name Marinol®.

Pain is the most frequently reported symptom and it is a common clinical problem confronting all clinicians. Millions of people in the United States suffer from severe pain that, according to numerous recent reports, is chronically under-treated or inappropriately managed. Similarly, millions of people also suffer from severe nausea and/or frequent emesis. Moreover, all too frequently, many patients suffering from chronic, under-treated or irretraceable pain also suffer from lack of appetite, nausea and/or frequent emesis. These patients present a greater clinical challenge as they are unable to receive effective doses of oral pain medications, thereby leaving their pain unalleviated. Cannabinoids, including cannabidiol, are effective in alleviating pain. Moreover, cannabinoids, including cannabidiol, can reduce a patient's nausea and vomiting, independent of any pain relief achieved. Thus, cannabinoids are particularly useful in patients experiencing nausea and vomiting secondary to un- or under-treated pain.

A notable percentage of the United States population satisfy the diagnostic criteria for alcohol use disorders ("AUDs"). The consumption of excessive amounts of alcohol results in a complex array of pharmacological effects that directly impact the ability to treat the condition. These effects directly impact the brain and include progressive neurodegeneration, impaired executive function and dependence leading to withdrawal-induced negative effects. It is known that cannabinoids, including cannabidiol, have neuroprotective, anxiolytic and anti-convulsant effects, which may be effective in preventing additional brain damage in persons with AUDs, while simultaneously decreasing the frequency of relapses.

Chronic abusers of *cannabis* can develop dependence and experience withdrawal symptoms when they attempt to discontinue use of the drug. Collectively, *cannabis* dependence and withdrawal are referred to herein as *cannabis* use disorders. It is known to those of skill in the art that cannabinoids, including cannabidiol, are useful in treating *cannabis* use disorders.

Dystonia is a neurological movement disorder, with many known causes, and characterized by involuntary, continual muscular contractions causing twisting and repetitive movements or abnormal postures. Cannabinoids have been shown to reduce the muscular contractions characteristic of this disorder.

The etiological pathology of many diseases relates to the inflammatory processes that are regulated by an individual's immune system. Inflammation may result from (1) an otherwise appropriate immunoresponse to an outside trauma, such as brain swelling secondary to a closed head injury; (2) an overactive immunoresponse, such as an allergic reaction or dermatitis; or (3) an inappropriate auto-immunoresponse, such as certain forms of multiple sclerosis, inflammatory bowel disorders and arthritis. Regardless of the underlying cause of the inflammation, it is therapeutically desirable under these circumstances to regulate the immune system and lessen the inflammatory response. Cannabinoids have been shown to regulate various steps in the immune response and could show some therapeutic benefit in the treatment of certain inflammatory diseases such as psoriatic arthritis.

Rheumatoid arthritis affects approximately 0.5-1% of the United States population, and autoimmune diseases in general affect more than 20 million Americans. The pain associated with rheumatoid arthritis can often be disabling. Cannabinoids have been found to be useful as an adjunct treatment for rheumatoid arthritis and joint pain secondary to other autoimmune diseases, such as inflammatory bowel disease, multiple sclerosis and systemic lupus erythematosus.

In addition, transdermally administered cannabinoids have been found to be useful to alleviate pain and other conditions associated with deeper tissues, such as peripheral nerves, muscles and synovial tissues. Examples of conditions associated with deeper tissues responsive to cannabinoids include: peripheral neuropathic pain, including but not limited to, the peripheral neuropathic pain associated with diabetic neuropathy, ankylosing spondylitis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, osteoarthritis, rheumatoid osteoarthritis, synovitis and juvenile rheumatoid arthritis. When cannabinoids are administered transdermally to treat pain and other conditions associated with deeper tissues, including peripheral neuropathic pain, it may be useful to have significant local tissue and systemic levels of cannabinoids.

In addition to the above-discussed therapeutics benefits, cannabinoids, such as cannabidiol and cannabidiol prodrugs, present a variety of pharmacological benefits, including, but not limited to, anti-inflammatory, anti-convulsant, anti-psychotic, antioxidant, neuroprotective, anti-cancer, such as melanoma, and immunomodulatory effects.

Given these systemic therapeutic benefits, it would be advantageous to develop a composition in which a cannabinoid, such as cannabidiol or a prodrug of cannabidiol, is delivered systemically to achieve therapeutically effective plasma concentrations in a patient. However, cannabinoid oral dosage forms, including those comprising cannabidiol, must overcome several obstacles in order to achieve a therapeutically-effective systemic concentration. First, cannabinoids are generally highly lipophilic. Their limited water solubility thereby restricts the amount of cannabinoid available for absorption in the gastrointestinal tract. Second, cannabidiol, as with the other cannabinoids, undergoes substantial first-pass metabolism when absorbed from the human gastrointestinal tract. Finally, the oral bioavailability of any product is further diminished when a patient suffers from nausea or emesis, as either the patient avoids taking his oral medications or the oral dosage form does not remain in the gastrointestinal tract for a sufficient period of time to release the entire dose and achieve a therapeutic concentration.

Therefore, in view of the foregoing, it would be desirable to systemically deliver therapeutically effective amounts of a cannabinoid, such as cannabidiol or cannabidiol prodrug, to a mammal in need thereof for the treatment of one or more medical conditions responsive to cannabinoids, including pancreatic cancer, pancreatitis, pain, nausea or appetite stimulation, by a route of administration that does not depend upon absorption from the gastrointestinal tract of the mammal. One non-oral route of administration for the systemic delivery of cannabidiol is transdermal administration.

In addition, the epidermis and dermis of many mammals, such as humans and guinea pigs, contains enzymes which are capable of metabolizing active pharmaceutical agents which pass through the stratum corneum. The metabolic process occurring in the skin of mammals, such as humans, can be utilized to deliver pharmaceutically effective quantities of a cannabinoid, such as cannabidiol, to the systemic circulation of a mammal in need thereof. Described herein are prodrugs of cannabinoids, such as cannabidiol prodrugs, and compositions comprising prodrugs of cannabinoids that can be transdermally administered to a mammal, such as a human, so that the metabolic product resulting from metabolism in the skin is the cannabinoid which is systemically available for the treatment of a medical condition responsive to cannabinoid, for example pancreatic diseases, such as pancreatitis and pancreatic cancer.

Unfortunately, due to its highly lipophilic nature, cannabidiol is poorly absorbed through membranes such as the skin of mammals, including humans. Therefore, the success of transdermally administering therapeutically effective quantities of cannabidiol to a mammal in need thereof within a reasonable time frame and over a suitable surface area has been substantially limited.

Microneedles and COX Inhibitors

Enhancing the transdermal delivery of an active pharmaceutical agent by use of microneedle treatment has become an important area of research in the field of transdermal drug delivery. In addition, shorter microneedles may alternatively be used to topically administer an active pharmaceutical agent for local delivery to treat dermal conditions. It has further been found that a pharmaceutical composition comprising a cannabinoid or cannabinoid prodrug and a penetration enhancer can be administered to a mammal in conjunction with a microneedle array to treat a medical condition responsive to cannabinoids, including alcohol use disorders and pancreatic diseases, such as pancreatic cancer and pancreatitis. To enhance the transdermal or topical delivery of cannabinoids when administered in conjunction with microneedles, cannabinoid prodrugs (e.g., cannabidiol prodrugs) have been designed which typically have a greater water solubility than the parent cannabinoid molecule in order to take advantage of the aqueous pores created by microneedle use.

Microneedles are generally considered to be structures that are between about 20 μm and about 1000 μm in length capable of puncturing the outermost layer of the epidermis (stratum corneum) to create large-scale openings (relative to the size of the active pharmaceutical agent to be delivered there through) or pores through which one or more active pharmaceutical ingredients can be delivered. The depth of microneedle penetration is sufficient to enhance transdermal drug delivery but not sufficient to stimulate nerve endings. Therefore, the use of microneedles is pain-free. This aspect, as well as their economical and easy use, makes a system incorporating microneedle technology an attractive alternative for transdermal drug delivery.

The active pharmaceutical agents to be delivered in conjunction with microneedle technology range from large oligonucleotides to insulin, and highly water-soluble compounds. Compared to other methods of physically altering the cutaneous structure to aid in improving transdermal transport, microneedle delivery is a relatively simple technique. Microneedles are typically micromachined to increase permeability and decrease skin sensation and come in various forms, such as biodegradable polymers, silicon and stainless steel. Various researchers have studied the effects of microneedle-treated skin on increased permeation of mostly water soluble compounds through microneedle-created aqueous pores. It has been shown that the use of microneedles can enhance the permeation of many compounds including non-viral gene therapy vectors, desmopressin, insulin and naltrexone. Further, the application of microneedles has been shown to be pain free in comparison to a 26-gauge hypodermic needle.

The effectiveness of microneedles is dependent on the duration of time that the microneedle-created pores in the stratum corneum remain sufficiently open and "un-healed." It is during this time that the enhanced delivery of the active pharmaceutical agent can continue. Recently there have been many determinations in pore lifetime and viability via a number of experiments involving transepidermal water loss, microscopic visualization and pharmacokinetic analysis. Transepidermal water loss ("TEWL") measures the rate at which water escapes from the skin. TEWL values are commonly measured in damaged skin to determine water loss over time as a function of skin repair. By using an evaporimeter, an instrument that measures water loss, damage or changes in skin morphology can be determined by an increase in rate of water loss compared to "normal" skin. It has now been shown that TEWL readings are a valid measurement to observe the status of the permeability barrier.

Occlusive coverings, such as patches or hydrogels (which can be optionally incorporated into a patch), can be used to maintain microneedle-created pores. When a microneedle array was placed on the skin and removed without having been treated with an occlusive patch, the skin healed rapidly and TEWL readings returned to baseline levels within 30 minutes. In contrast, it has been demonstrated that under an occlusive environment, microneedle-created pores remained open for at least 48-72 hours. Likewise, microscopic visualization after staining has revealed that pores were present up to 72 hours. In hairless guinea pigs treated with 6-β-naltrexol hydrochloride, significant enhancement in microneedle pore viability was observed for 48 hours after microneedle exposure and occlusion, compared to untreated skin. It has also been shown that therapeutic levels of naltrexone (2.5±1.1 ng/mL) were achieved when a 16% naltrexone hydrochloride gel was administered to 6 healthy human volunteers after microneedle pretreatment. Further, it has been observed that when used in conjunction with microneedles, steady state naltrexone concentrations were achieved within two hours and remained for 48 hours. These results indicate that microneedle application to skin provides an alternative delivery route to oral, injectables and traditional passive transdermal delivery.

Even with the use of occlusive techniques (e.g., a patch which may optionally have a hydrogel incorporated therein) in conjunction with the microneedle-generated pores, it is, nevertheless, desirable to further extend the lifetime of microneedle-created pores. Such an increase in the duration of the pore opening can correspond to an increase in the interval between which doses are administered. Said differently, by increasing the duration of the pore opening, it is possible to reduce the frequency with which an active must be administered. Reductions in the dosage frequency have a positive impact on patient acceptance and compliance. Thus, it would be desirable to further enhance the viability of the microneedle-created pores in order to increase the rate, duration and extent of transdermal delivery of an active pharmaceutical agent.

It has been found that the rate and extent of cannabinoid transdermal absorption can be improved by administering a cannabinoid (e.g. cannabidiol) or a cannabinoid prodrug (e.g., a prodrug of cannabidiol) and optionally a penetration enhancer or co-solvent and/or a COX inhibitor, in pharmaceutical compositions in conjunction with microneedle arrays. It has further been discovered that by optimizing the composition excipients, the cannabinoid or cannabinoid prodrug can be administered, in conjunction with a microneedle array, on a schedule that encourages patient compliance, by reducing frequency of dosing to once or twice daily or even once or twice weekly.

Accordingly, a significant advancement in the art would occur with the development of a transdermal drug delivery system comprising pharmaceutical compositions, comprising a cannabinoid (e.g. cannabidiol) or a cannabinoid prodrug (e.g., a prodrug of cannabidiol), and a microneedle array in treatment of conditions responsive to cannabinoids. A further advancement would be the development of a transdermal drug delivery system comprising a pharmaceutical composition, comprising a cannabinoid (e.g. cannabidiol) or a cannabinoid prodrug (e.g., a prodrug of cannabidiol) and a microneedle array in treatment of (i) acute pancreatitis; (ii) chronic pancreatitis; (iii) pancreatic cancer; (iv) pain; (v) inflammation or (vi) alcohol use disorders.

Topical Delivery

In addition to the benefits of systemically administered cannabinoid discussed above, cannabinoids, including cannabidiol and prodrugs of cannabidiol, have been found to have localized benefits from topical administration. For example, topically administered cannabinoids have been found to be useful to alleviate pain and other conditions originating at or near the surface of the skin, including but not limited to, pain associated with post-herpetic neuralgia, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, melanoma and psoriatic arthritis. Also, it has been found that the topical administration of cannabinoids, including cannabidiol, can inhibit the growth of hair.

In order to achieve these local benefits, it may be advantageous for the cannabinoid, (e.g., cannabidiol) or a cannabinoid prodrug (e.g., a cannabidiol prodrug) to penetrate the stratum corneum but not be absorbed systemically. In such a case, the cannabinoid (e.g., cannabidiol) or cannabinoid prodrug (e.g., a prodrug of cannabidiol) would concentrate in the skin and/or pilosebaceous unit, thus maximizing its local effect. Not only does the localized effect increase the potential therapeutic benefit, it lessens the frequency and severity of side-effects associated with systemic cannabinoid administration because the amount of active compound circulating in the patient is reduced. The cannabinoid (e.g., cannabidiol) or cannabinoid prodrug (e.g., a cannabidiol prodrug) can be incorporated into a composition with an additional active moiety that is capable of improving the appearance and/or hydration of the skin.

Accordingly, a significant advancement in the art would occur with the development of a topical drug delivery system comprising a pharmaceutical composition, comprising a cannabinoid (e.g., cannabidiol) or a cannabinoid prodrug (e.g., a cannabidiol prodrug) and a microneedle array in the treatment of condition responsive to cannabinoid therapy.

SUMMARY

Described herein are microneedle drug delivery systems suitable for transdermal and topical administration comprising a pharmaceutical composition, comprising a cannabinoid (e.g., cannabidiol) or a cannabinoid prodrug (e.g., a cannabidiol prodrug) and a microneedle array. Also described herein are methods of using a microneedle transdermal or topical drug delivery system for administering pharmaceutical compositions comprising a cannabinoid (e.g., cannabidiol) or a cannabinoid prodrug (e.g., a cannabidiol prodrug) and a microneedle array in the treatment of diseases in mammals.

Some alternative embodiments also include the use of a hydrogel as part of the drug delivery system.

Other embodiments, objects, features and advantages will be set forth in the detailed description of the embodiments that follows, and in part will be apparent from the description or may be learned by practice of the claimed invention. These objects and advantages will be realized and attained by the processes and compositions described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

FIG. 1 shows the cumulative permeation profile of total CBD (total cannabidiol equivalents delivered in the form of cannabidiol and/or prodrugs ALL00179 and ALL00180) from ALL00179 (n=5) in 100% ddH$_2$O donor solution through microneedle-treated Yucatan pig skin.

DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading. Embodiments disclosed herein are inclusive and exclusive of other embodiments.

Transdermal and Topical Drug Delivery Systems

One embodiment described herein includes microneedle transdermal or topical drug delivery systems comprising a microneedle array and a pharmaceutical composition, wherein the pharmaceutical composition comprises a cannabinoid (e.g., cannabidiol) or a cannabinoid prodrug (e.g., a cannabidiol prodrug). In a further embodiment, the microneedle transdermal or topical drug delivery system comprises a microneedle array and a pharmaceutical composition, wherein the composition comprises a cannabinoid (e.g., cannabidiol) or a cannabinoid prodrug (e.g., a cannabidiol prodrug) and a COX inhibitor. In yet a further embodiment, the microneedle transdermal or topical drug delivery system comprises a microneedle array and a pharmaceutical composition, where in the composition comprises a cannabinoid (e.g., cannabidiol) or a cannabinoid prodrug (e.g., a cannabidiol prodrug) and a penetration enhancer or co-solvent. In yet a further embodiment, the microneedle transdermal or topical drug delivery system comprises a microneedle array and a pharmaceutical composition, where in the composition comprises a cannabinoid (e.g., cannabidiol) or a cannabinoid prodrug (e.g., a cannabidiol prodrug), a COX inhibitor and a penetration enhancer or co-solvent.

In one embodiment described herein, the microneedle transdermal or topical drug delivery system comprises a pharmaceutical composition and a microneedle array. In another embodiment described herein, administration of the transdermal or topical drug delivery system means that the pharmaceutical composition is applied or administered to the skin of a mammal in conjunction with the microneedle array. As used herein "in conjunction with" means use before, use after or use simultaneously. For example, administration of a transdermal or topical drug delivery system comprising a pharmaceutical composition in conjunction with a microneedle array means that the pharmaceutical composition may be administered before the administration of the microneedle array, after the administration of the microneedle array or simultaneously with the administration of the microneedle array.

In another embodiment described herein, the microneedle transdermal or topical drug delivery system described herein comprises a pharmaceutical composition comprising a cannabinoid (e.g., cannabidiol) or a cannabinoid prodrug (e.g., a cannabidiol prodrug) in conjunction with a microneedle array for the treatment of a disease or condition responsive to a cannabinoid.

In another embodiment described herein, the microneedle transdermal or topical drug delivery system described herein comprises a pharmaceutical composition comprising a cannabinoid (e.g., cannabidiol) or a cannabinoid prodrug (e.g., a cannabidiol prodrug) incorporated into a hydrogel which is used in conjunction with a microneedle array.

In another embodiment described herein, the microneedle transdermal or topical drug delivery system described herein comprises a pharmaceutical composition comprising a cannabinoid (e.g., cannabidiol) or a cannabinoid prodrug (e.g., a cannabidiol prodrug) incorporated into a hydrogel which is used in conjunction with a microneedle array for the treatment of a disease or condition responsive to a cannabinoid.

In another embodiment, the microneedle transdermal or topical drug delivery system consists essentially of a microneedle array and a pharmaceutical composition, wherein the pharmaceutical composition consists essentially of a cannabinoid (e.g., cannabidiol) or a cannabidiol prodrug (e.g., a cannabidiol prodrug) and optionally further consists essentially of a COX inhibitor and/or a penetration enhancer (i.e., a co-solvent).

In another embodiment, the microneedle transdermal or topical drug delivery system consists of a microneedle array and a pharmaceutical composition, wherein the pharmaceutical composition consists of a cannabinoid (e.g., cannabidiol) or a cannabidiol prodrug (e.g., a cannabidiol prodrug) and optionally further consists of a COX inhibitor and/or a penetration enhancer (i.e., a co-solvent).

Cannabinoids, Cannabidiol and Cannabidiol Prodrugs

As used herein, "cannabinoid" includes any compound that interacts with a cannabinoid receptor and various cannabinoid mimetics, including, but not limited to certain tetrahydropyran analogs (e.g., delta-9-tetrahydrocannabinol; delta-8-tetrahydrocannabinol, 6,6,9-trimethyl-3-pentyl-6H-dibenzo[b,d]pyran-1-ol; 3-(1,1-dimethylheptyl)-6,6a,7,8,10,10a-hexahydro-1-hydroxy-6,6-dimethyl-9H-dibenzo[b,d]pyran-9-one; (−)-(3S,4S)-7-hydroxy-delta-6-tetrahydrocannabinol-1,1-dimethylheptyl; (+)-(3S,4S)-7-hydroxy-delta-6-tetrahydrocannabinol-1,1-dimethylheptyl; 11-hydroxy-delta-9-tetrahydrocannabinol and delta-8-tetrahydrocannabinol-11-oic acid); certain piperidine analogs (e.g., (−)-(6S,6aR,9R,10aR)-5,6,6a,7,8,9,10,10a-octahydro-6-methy-1-3-[(R)-1-methyl-4-phenylbutoxy]-1,9-phenanthridinediol 1-acetate), certain aminoalkylindole analogs (e.g., (R)-(+)[2,3-dihydro-5-methyl-3-(4-morpholinylmethyl)-pyrrolo[1,2,3-de]-1,4-benzoxazin-6-yl]-1-naphthalenyl-methanone), certain open pyran-ring analogs (e.g., 2-[3-methyl-6-(1-methylethenyl)-2-cyclohexen-1-yl]-5-pentyl-1,3-benzenedi-ol and 4-(1,1-dimethylheptyl)-2,3'-dihydroxy-6'alpha-(3-hydroxypropyl)-1',-2',3',4',5',6'-hexahydrobiphenyl), and their pharmaceutically acceptable salts, solvates, metabolites (e.g., cutaneous metabolites), and metabolic precursors (e.g., prodrugs).

As used herein, "cannabidiol" refers to cannabidiol; cannabidiol prodrugs; pharmaceutically acceptable derivatives of cannabidiol, including pharmaceutically acceptable salts of cannabidiol; and cannabidiol derivatives. As used herein "cannabidiol prodrug" means a compound that undergoes a chemical conversion, through a metabolic process or otherwise within the body of the mammal receiving the compound into cannabidiol. The term "cannabidiol prodrug" also includes the free base, free acid, salt, ester, hydrate, anhydrate, amide, enantiomer, isomer, tautomer, polymorph, or derivative of a compound that undergoes a chemical conversion, through a metabolic process or otherwise within the body of the mammal receiving the compound into cannabidiol.

In one embodiment described herein, the cannabinoid or mixture of cannabinoids, is obtained from the extract from of a natural source, such as plants from the *cannabis* genus (e.g., *Cannabis sativa, Cannabis indicia and Cannabis ruderalis*). In an alternative embodiment, the cannabinoid or mixture of cannabinoids results from synthetic chemical reactions. The synthesis of cannabidiol can be found in Petilka et al., Helv. Chim. Acta, 52:1102 (1969) and in Mechoulam et al., J. Am. Chem. Soc., 87:3273 (1965), which are hereby incorporated by reference. In a further embodiment, the cannabinoid or mixture of cannabinoids, is obtained from the extract from of a natural source, such as plants from the *cannabis* genus and not as a result of synthetic chemical reactions. In yet another embodiment, the cannabinoid or mixture of cannabinoids results from synthetic chemical reactions and not from the extract of a natural source, such as plants from the *cannabis* genus.

A cannabinoid may be in any suitable form for administration to a mammal such as in the form of a free base, free acid, salt, hydrate, anhydrate, enantiomer, isomer, tautomer, polymorph, or the like, provided that the form of the cannabinoid is therapeutically active or undergoes conversion within or outside of the body to a therapeutically active form of the cannabinoid.

"Pharmaceutically acceptable salts," or "salts," include the salt of the parent molecule, such as cannabinoid or a cannabinoid prodrug, suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, beta-hydroxybutyric, galactaric and galacturonic acids. The following list of pharmaceutically acceptable salts is not meant to be exhaustive but merely illustrative as a person of ordinary skill in the art would appreciate that other pharmaceutically acceptable salts of a cannabinoid and prodrugs of a cannabinoid may be prepared.

In one embodiment, acid addition salts are prepared from the free base forms using conventional methodologies involving reaction of the free base with a suitable acid. Suitable acids for preparing acid addition salts include both organic acids, e.g., formic acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as a person of ordinary skill in the art would appreciate that other acids may be used to create pharmaceutically acceptable salts of prodrugs of cannabidiol. In still other embodiments, the basic salts are alkali metal salts, e.g., sodium salt.

In a further embodiment, the cannabinoid is substantially free from impurities. As used herein, "substantially free of impurities" shall mean that impurities, including any cannabinoid not intended to be administered in a therapeutically effective quantity, are present in an amount by weight of the composition of less than about 10%, less than about 5%, less than about 4%, less than about 3%, less than about 2%, less than about 1%, or less than about 0.1%.

As used herein "prodrug" refers to a compound that undergoes a chemical conversion, through a metabolic process or otherwise within the body of the mammal receiving the compound into its active form that has therapeutic effects. As used herein, the terms "cannabidiol" and "cannabidiol prodrug" are used interchangeably, such that any embodiment in which cannabidiol is used, may also be used with one or more cannabidiol prodrugs.

In one embodiment, illustrative cannabidiol prodrugs include those compounds of Formula (I):

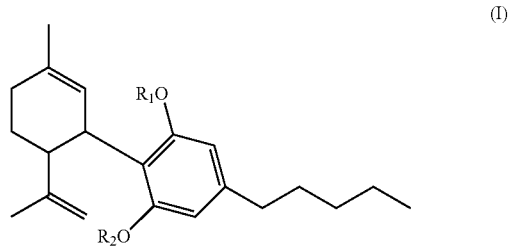

(I)

wherein $R_1$ and $R_2$ can be the same or different and are each independently comprised of a hydrogen and/or a bio-labile linker (e.g., ester, oxygenated ester, oxaester, pegylated ester, hydroxylated ester, alkyl ester, amino ester, alkylamino ester, dialkylamino ester, trialkylammonium ester, carbonate, alkyl carbonate, amino carbonate, alkylamino carbonate, dialkylamino carbonate, trialkylammonium carbonate, carbamate, alkyl carbamate, amino carbamate, alkylamino carbamate, dialkylamino carbamate, trialkylammonium carbamate, substituted phosphate ester, unsubstituted phosphate ester, unsubstituted diphosphate ester, substituted diphosphate ester, unsubstituted triphosphate ester, substituted triphosphate ester, phosphonate ester, substituted sulfate esters, unsubstituted sulfate esters, sulphonate ester, alpha-acyloxyalkyl, alpha-phosphoryloxyalkyl, alpha-sulphonyloxyalkyl or other suitable bio-labile linking structure) and further comprising moieties which can be selected in order to control the rate and extent of absorption and metabolism, including transdermal absorption and metabolism. However, $R_1$ and $R_2$ cannot both be a hydrogen atom. Several options for $R_1$ and $R_2$ are disclosed herein. Also included herein is the free base, free acid, salt, ester, hydrate, amide, enantiomer, isomer, tautomer, polymorph, or derivative thereof of compounds of Formula I.

In a further embodiment, the cannabidiol prodrug can be selected from a group comprising:

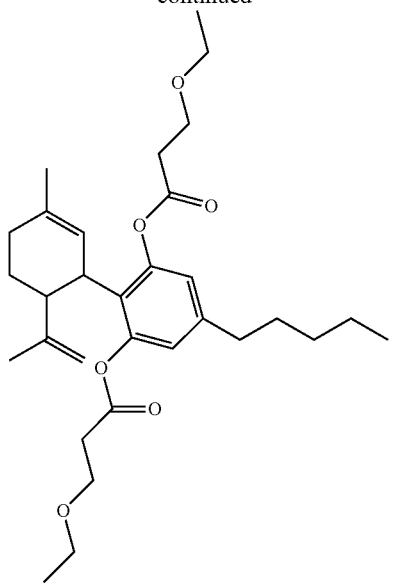

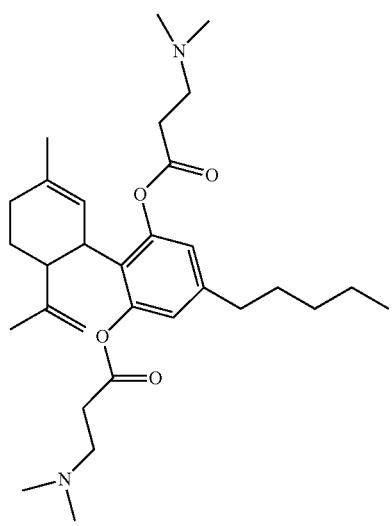

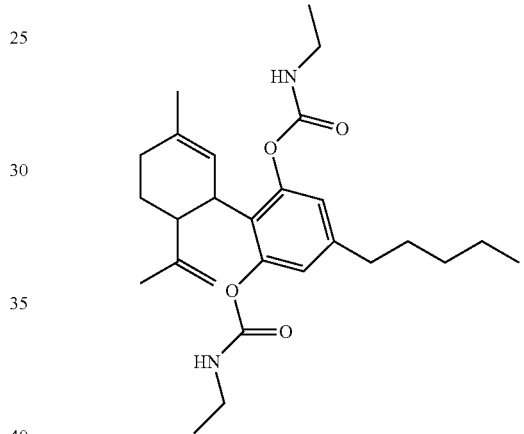

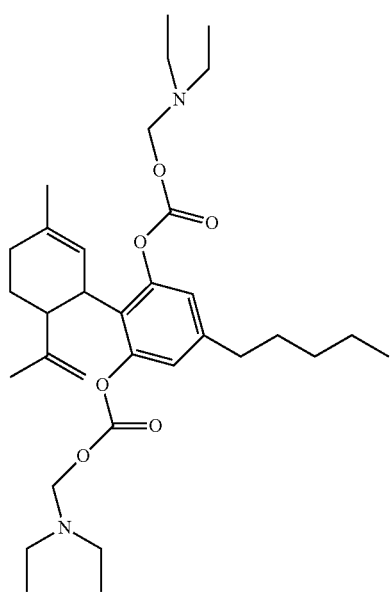

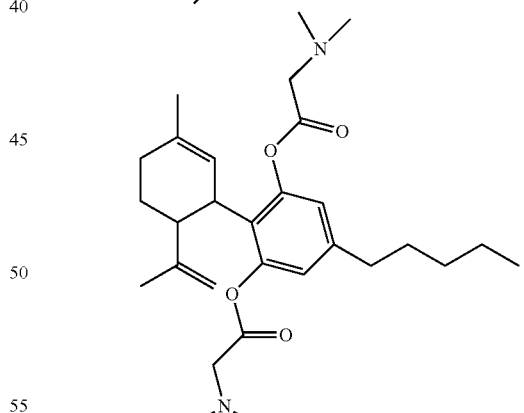

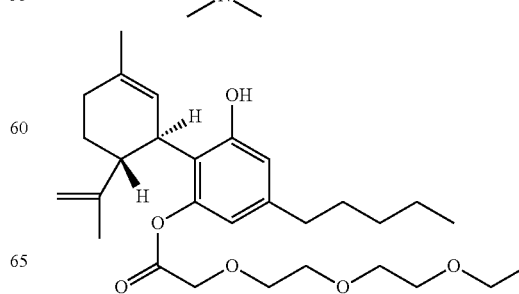

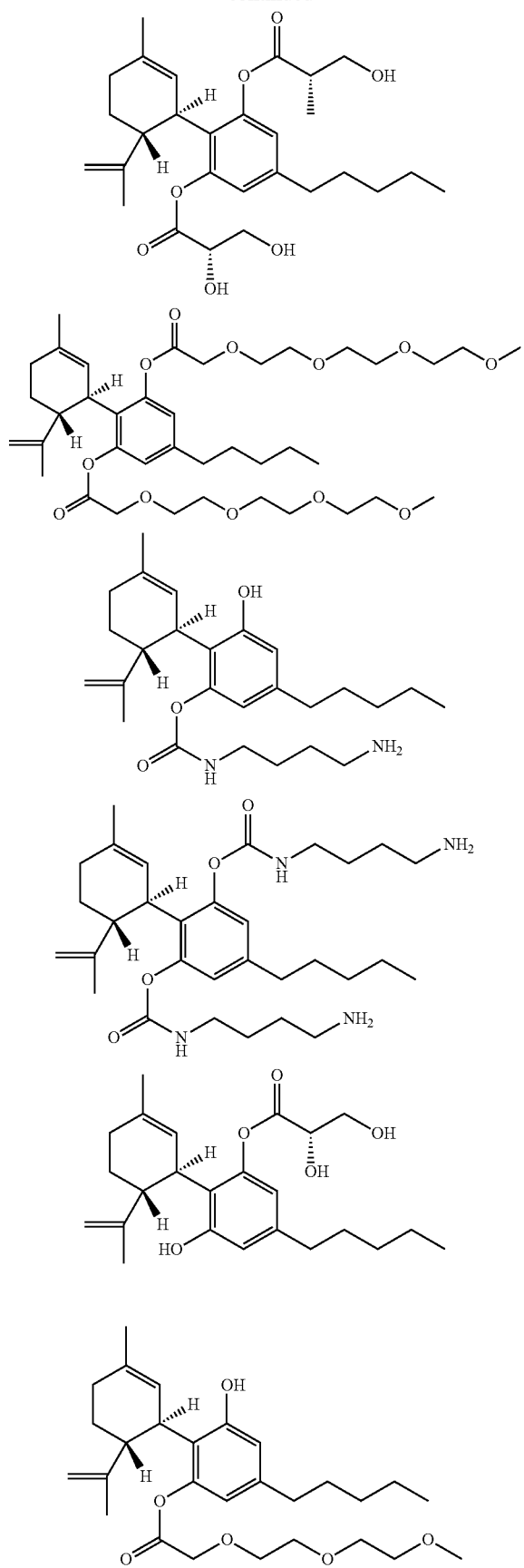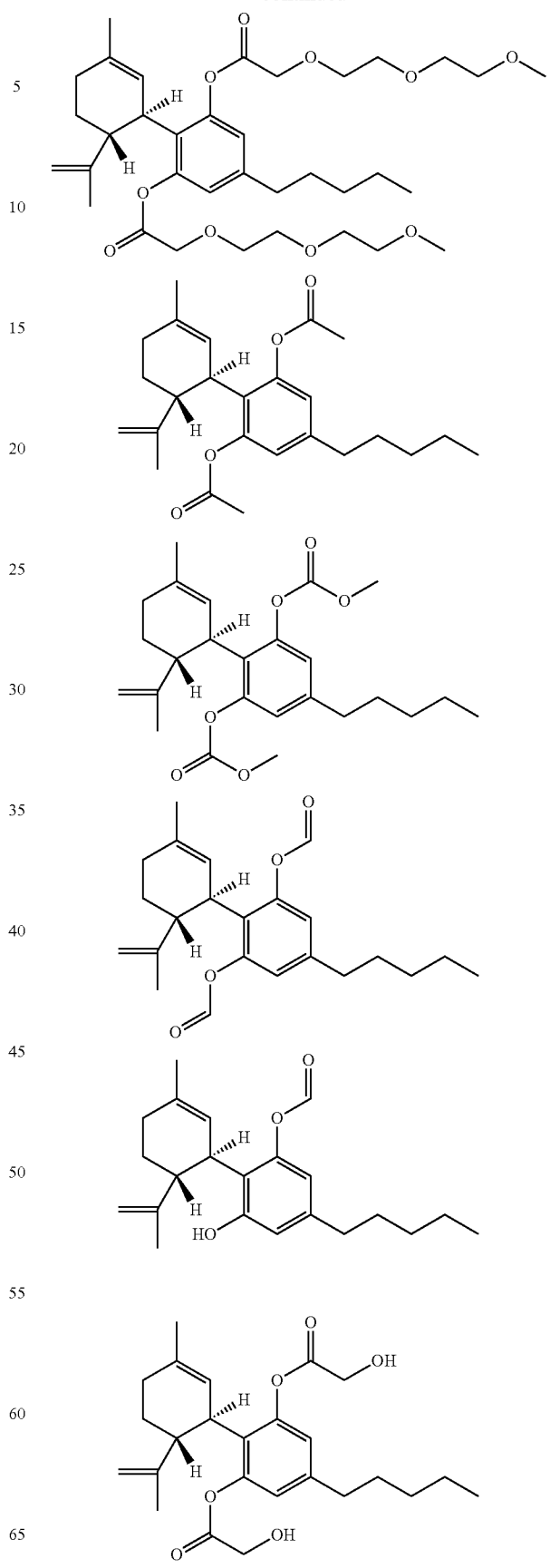

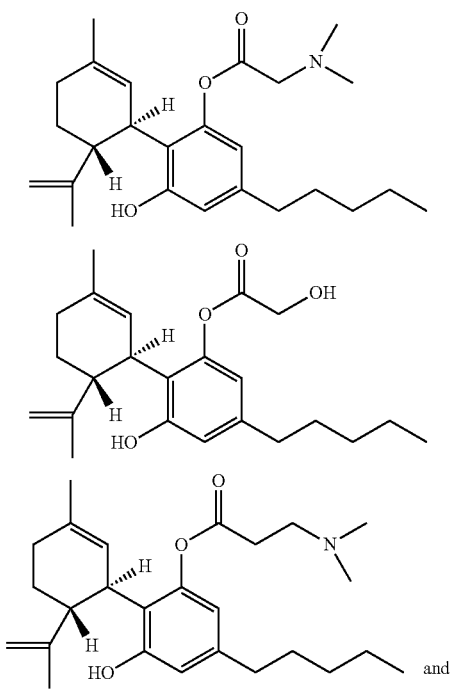

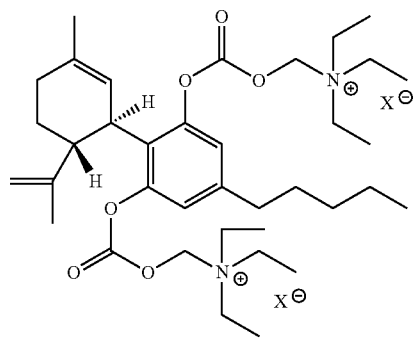

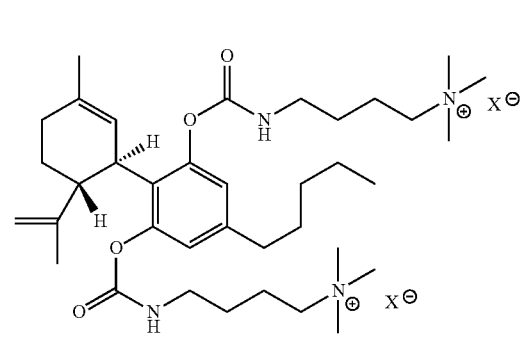

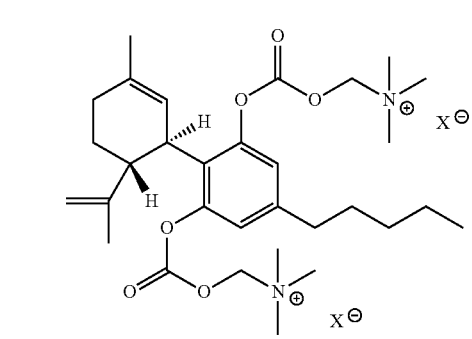

In an additional embodiment, cannabidiol prodrugs bearing an alkylamino or dialkylamino substituent in the side chain are used in the form of tetraalkylammonium salts. For example, dialkylamino ester can be used in the form of trialkylammonium ester. These separate chemical entities include a counter ion derived from pharmaceutically acceptable acids.

In one embodiment of the quaternary ammonium derivatives (tetraalkylammonium ammonium derivatives), the cannabidiol prodrug can be selected from a group comprising:

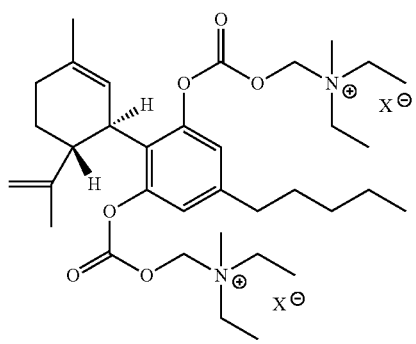

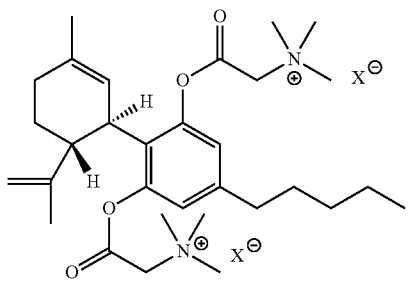

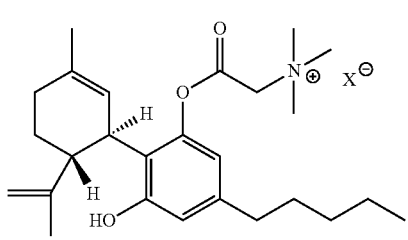

-continued

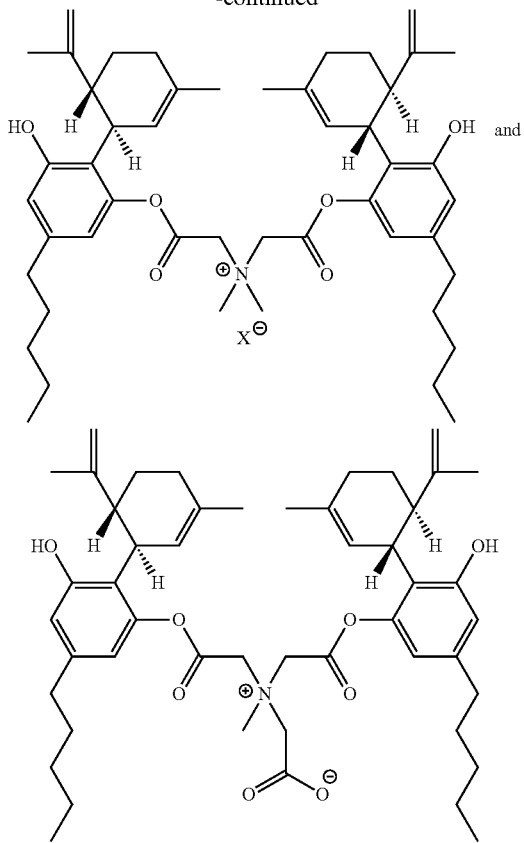

wherein X⁻ is a counter ion derived from pharmaceutically acceptable acids.

In a further embodiment, one or more cannabidiol prodrugs can be used with or instead of cannabidiol or other cannabinoids in the pharmaceutical compositions and drug delivery systems described herein. In an additional embodiment, a cannabidiol prodrug can be used with or instead of cannabidiol or other cannabinoids in the method of administering cannabidiol to mammal described herein.

Additional embodiments of cannabidiol prodrugs contemplated by the present disclosure include, but are not limited to, those described in U.S. patent application Ser. No. 12/182,974, published as US 2009-0036523 A1 on Feb. 5, 2009, which is incorporated herein by reference in its entirety.

In one embodiment, illustrative $\Delta^9$-tetrahydrocannabidiol prodrugs suitable for use in the compositions, drug delivery systems and methods described herein include those compounds of Formula (II):

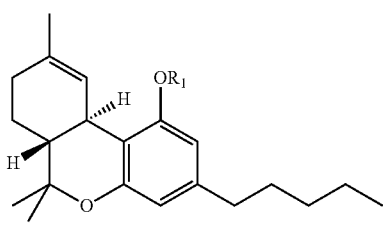

wherein $R_1$ is comprised of a bio-labile linker (e.g. ester, oxygenated ester, oxaester, pegylated ester, hydroxylated ester, branched hydroxylated ester, succinic acid monoester, oxalic acid mixed pegylated ester, amino ester, cyclic amino ester, acylated amino ester, carbonate, oxygenated carbonate, oxacarbonate, pegylated carbonate, hydroxylated carbonate, branched hydroxylated carbonate, aminoalkyl carbonate, cyclic aminoalkyl carbonate, acylated aminoalkyl carbonate, hydroxycarbonylalkyl carbonate, carbamate, alkyl carbamate, aminoalkyl carbamate, acylated aminoalkyl carbamate, cyclic aminoalkyl carbamate, oxacarbamate, pegylated carbamate, hydroxylated carbamate, branched hydroxylated carbamate, hydroxycarbonylalkyl carbamate, phosphate, diphosphate, triphosphate or other suitable biolabile linking structure) and further comprising moieties which can be selected in order to control the rate and extent of absorption and metabolism, such as transdermal absorption and metabolism. Several options for R.sub.1 are disclosed herein. Also included herein is the free acid, free base, salt, ester, hydrated forms, anhydrous, amide, enantiomer, isomer, tautomer, polymorph, or derivative thereof of compounds of Formula II.

In one embodiment, the pharmaceutical compositions disclosed herein comprise a cannabinoid, such as cannabidiol or cannabidiol prodrug, in a total amount by weight of the composition of about 0.1% to about 95%. For example, the amount of a cannabinoid, such as cannabidiol or a cannabidiol prodrug, by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Illustratively, the pharmaceutical compositions disclosed herein may comprise a total amount of a cannabinoid, such as cannabidiol or a cannabidiol prodrug, by weight of about 1% to about 10%; about 2% to about 10%; about 3% to about 10%; about 4% to about 10%; about 5% to about 10%; about 6% to about 10%; about 7% to about 10%; about 8% to about 10%; about 9% to about 10%; about 1% to about 9%; about 2% to about 9%; about 3% to about 9%; about 4% to about 9%; about 5% to about 9%; about 6% to about 9%; about 7% to about 9%; about 8% to about 9%; about 1% to about 8%; about 2% to about 8%; about 3% to about 8%; about 4% to about 8%; about 5% to about 8%; about 6% to about 8%; about 7% to about 8%; about 1% to about 7%; about 2% to about 7%; about 3% to about 7%; about 4% to about 7%; about 5% to about 7%; about 6% to about 7%; about 1% to about 6%; about 2% to about 6%; about 3% to about 6%; about 4% to about 6%; about 5% to about 6%; about 1% to about 5%; about 2% to about 5%; about 3% to about 5%; about 4% to about 5%; about 1% to about 4%; about 2% to about 4%; about 3% to about 4%; about 1% to about 3%; about 2% to about 3%; or about 1% to about 2%.

In an alternative embodiment, the pharmaceutical compositions disclosed herein comprise a cannabinoid (e.g., cannabidiol) or a prodrug of a cannabinoid (e.g., a prodrug of cannabidiol) which may be incorporated into a hydrogel. Optionally, a penetration enhancer (i.e., co-solvent) or COX inhibitor may also be incorporated into the hydrogel as well. The cannabinoid or prodrug thereof comprises about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 55%, about 60%, about 65%, about 70%, about 75%, about 80%, about 85%, about 90% or about 95% by weight of the hydrogel.

Microneedle Arrays

As used herein, the term "pore viability" refers to pores, holes or channels created by the entry of one or more microneedles into the skin of a mammal in need of transdermal administration of an active pharmaceutical agent and the duration of lifetime that the resulting pores remain sufficiently open or "un-healed" thereby allowing the transdermal delivery of an active pharmaceutical agent to be systemically or locally delivered, whereby the dosing interval between microneedle treatments can be extended.

As used herein the term "microneedle" or "microneedle array" refers to any apparatus, construction, equipment, implement, material, means or mechanism used to create micrometer-scale transport pathways in the epidermis of a mammal. As used herein, the terms "microneedle" and "microneedle array" are interchangeable.

The pharmaceutical compositions described herein, and optionally incorporated into a hydrogel, are suitable for use in a transdermal or topical drug delivery system in conjunction with microneedles which create micrometer-scale transport pathways. Microneedles provide a minimally invasive means to transport molecules into and/or through the skin for local or systemic delivery of an active pharmaceutical agent. The channels or pores created by a microneedle array are extremely small on a clinical level. However, because the channels or pores are orders of magnitude larger than even macromolecules, such channels or pores have been shown to significantly increase skin permeability.

Microneedles can be can be solid or hollow and are made from many bio-compatible materials, including silicon, bio-degradable polymers, and stainless steel. Solid microneedles can be used to create channels or pores in the skin, followed by application of a transdermal patch to the skin surface. Alternatively, solid microneedles can be first coated with an active pharmaceutical agent and then inserted into the skin. Hollow microneedles can also be used to facilitate active permeation through the bore in the microneedle and into the skin. See, e.g., Prausnitz, Microneedles for transdermal drug delivery, Adv. 56 Drug. Deliv. Rev. 581-587 (2004), for a review of some of the microneedle technology suitable for use with the various embodiments of the claimed invention described herein.

Numerous studies have demonstrated that solid microneedles can increase skin permeability by up to four orders of magnitude for compounds ranging in size from small molecules to proteins to nanoparticles. Henry et al., Microfabricated microneedles: a novel approach to transdermal drug delivery, 87 J. Pharm. Sci. 922-925 (1998); McAllister et al., Microfabricated needles for transdermal delivery of macromolecules and nanoparticles: fabrication methods and transport studies, 100 Proc. Nat'l Acad. Sci. 13755-13760 (2003); Lin et al., Transdermal delivery of antisense oligonucleotides with microprojection patch (Macroflux) technology, 18(12) Pharm. Res. 1787-1793 (2001); and Cormier et al., Transdermal delivery of desmopressin using a coated microneedle array patch system, 97 J. Control. Release. 503-511 (2004). Hollow microneedles have also been shown to deliver macromolecules such as insulin. See McAllister, Proc. Nat'l Acad. Sci. 13755-13760; Martanto et al., Transdermal delivery of insulin using microneedles in vivo, 21 Pharm. Res. 947-952 (2004). Microneedle insertion in human volunteers resulted in a sensation described as that similar to a smooth surface applied to the skin or the "sensation of a piece of tape" applied to the skin. Kaushik et al., Lack of pain associated with microfabricated microneedles, 92 Anesth. & Analg. 502-504 (2001).

Suitable microneedle arrangements for use with the compounds and compositions described herein can be found in the foregoing references as well as in U.S. patent application Ser. No. 11/812,249, published as US 2008-0008745 A1 on Jan. 10, 2008, which is incorporated by reference herein in its entirety.

In one embodiment, solid microneedle adhesive patches can be fabricated for insertion into the skin. In another embodiment, fixed microneedle geometries can be cut into 75 μm thick stainless steel sheets (Trinity Brand Industries, SS 304; McMaster-Carr, Atlanta, Ga., USA) using an infrared laser (Resonetics Maestro, Nashua, N.H., USA) and then can be manually bent perpendicular to the plane of their metal substrate. For better insertion and adhesion of patches to the skin, microneedle arrays can be assembled into adhesive patches. The adhesive would serve to hold the microneedles firmly against the skin by compensating for the mechanical mismatch between the flexible skin tissue and the rigid microneedle substrate. The microneedle patches can be assembled in a laminar flow hood for cleanliness and then sterilized using ethylene oxide (AN 74j, Andersen Sterilizers, Haw River, N.C., USA) before use.

In another embodiment, microneedle arrays can be fabricated to produce patches containing 50 microneedles arranged in a 5×10 array of microneedles. In one embodiment, suitable individual microneedles can be about 620 μm in length, about 160 μm in width at the base, and less than about 1 μm in radius of curvature at the tip.

Pharmaceutical Compositions

As used herein, "pharmaceutical composition" includes any ointment, cream, solution, suspension, lotion, paste, gel, hydrogel, spray, foam, solid or oil which may be created or formed and used to administer a cannabinoid (e.g., cannabidiol) or cannabinoid prodrug (e.g., a cannabidiol prodrug) to a mammal, alone, or in conjunction with microneedles.

As used herein, the terms "gel" or "gel-like" can be used interchangeably.

The term "excipient" herein means any substance, not itself a therapeutic agent, which may be used in a composition for delivery of an active therapeutic agent to a subject or combined with an active therapeutic agent (e.g., to create a pharmaceutical composition) to improve its handling or storage properties or to permit or facilitate formation of a dose unit of the composition (e.g., formation of a hydrogel which may then be optionally incorporated into a patch). Excipients include, by way of illustration and not limitation, binders, disintegrants, taste enhancers, solvents, thickening or gelling agents (and any neutralizing agents, if necessary), penetration enhancers, solubilizing agents, wetting agents, antioxidants, lubricants, emollients, substances added to mask or counteract a disagreeable odor, fragrances or taste, substances added to improve appearance or texture of the composition and substances used to form hydrogels. Any such excipients can be used in any dosage forms according to the present disclosure. The foregoing classes of excipients are not meant to be exhaustive but merely illustrative as a person of ordinary skill in the art would recognize that additional types and combinations of excipients could be used to achieve the desired goals for delivery of the cannabinoid (e.g., cannabidiol) or cannabinoid prodrug (e.g., a cannabidiol prodrug).

The pharmaceutical compositions described herein are suitable for transdermal or topical administration. In one embodiment, the microneedle transdermal or topical drug delivery system comprises a microneedle array and a pharmaceutical composition, wherein the pharmaceutical composition comprises a cannabinoid (e.g., cannabidiol) or a cannabinoid prodrug (e.g., a cannabidiol prodrug) which has been optionally incorporated into a hydrogel. In further embodiments, the pharmaceutical composition may comprise a COX inhibitor which has been optionally incorporated into a hydrogel. In further embodiments, the pharmaceutical composition may optionally further comprise on or more pharmaceutically acceptable excipients such as solvents, co-solvents, thickening agents, neutralizers, solubilizing agents, wetting agents, penetration enhancers, lubricants, emollients, antioxidants, substances added to mask or counteract a disagreeable odor, fragrances or tastes, and substances added to improve appearance or texture of the composition. In a further embodiment, the pharmaceutical composition can be part of, or incorporated into, a hydrogel.

COX Inhibitors

It has been found that certain compounds can be administered to mammals to prevent or reduce prostaglandin biosynthesis in mammals by inhibiting the production of prostaglandin G/H synthase which is also known as cyclooxygenase or COX. There are two forms of cyclooxygenase, cyclooxygenase-1 (COX-1) and cyclooxygenase-2 (COX-2). As used herein, the term "COX inhibitor" includes those compounds which (i) primarily or exclusively inhibit the COX-1 enzyme; (ii) primarily or exclusively inhibit the COX-2 enzyme; and (iii) those compounds which inhibit both the COX-1 and COX-2 enzymes (i.e., non-specific inhibitors). COX-1, COX-2 and non-specific COX inhibitors are each suitable for use in the compositions, drug delivery systems and methods described herein.

Examples of COX inhibitors suitable for use in the various embodiments described herein include: aspirin, diflunisal, olsalazine, salsalate, sulfasalazine, acetaminophen, indomethacin, sulindac, etodolac, mefenamic acid, meclofenamate, flufenamic acid, tolmetin, ketorolac, diclofenac, ibuprofen, naproxen, fenoprofen, ketoprofen, flurbiprofen, oxaprozin, piroxicam, meloxicam, nabumetone, celecoxib, valdecoxib, rofecoxib, parecoxib, etoricoxib, lumiracoxib, valdecoxib, nimesulide, mofezolac, SC-560, FR122047, and DuP-697. Additional COX inhibitors can be found in Merck Index, Thirteenth Ed., The Physicians Desk Reference, 58$^{th}$ Ed., and Goodman and Gilmans, "The Pharmacological Basis of Therapeutics, 11th Ed.

Pharmaceutically acceptable forms of a COX inhibitor include those which are suitable for transdermal or topical administration to a mammal. The COX inhibitors described herein may be in any form suitable for administration to a mammal, such as in the form of a free base, free acid, salt, ester, hydrate, anhydrate, enantiomer, isomer, tautomer, polymorph, derivative, or the like.

Pharmaceutically acceptable salts of a COX inhibitor include salts suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, beta-hydroxybutyric, galactaric and galacturonic acids. The following list of pharmaceutically acceptable salts is not meant to be exhaustive but merely illustrative as a person of ordinary skill in the art would appreciate that other pharmaceutically acceptable salts of a COX inhibitor may be prepared.

In one embodiment, acid addition salts can be prepared from the free base forms through a reaction of the free base with a suitable acid. Suitable acids for preparing acid addition salts of COX inhibitors include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as a person of ordinary skill in the art would appreciate that other acids may be used to create pharmaceutically acceptable salts of a COX inhibitor. In other embodiments, an acid addition salt is reconverted to the free base by treatment with a suitable base. In still other embodiments, the basic salts are alkali metal salts, e.g., sodium salt.

One embodiment described herein is a microneedle transdermal or topical drug delivery system, which includes a pharmaceutical composition comprising a cannabinoid (e.g., cannabidiol) or a cannabinoid prodrug (e.g., a prodrug of cannabidiol), and a first COX inhibitor, and a microneedle array which is arranged to penetrate the skin of a mammal in need of for transdermal or topical delivery of the cannabinoid to treat a medical condition. In other embodiments, the COX inhibitor is a COX-1 inhibitor. In a further embodiment, the COX inhibitor is a COX-2 inhibitor. In another embodiment, the COX inhibitor is both a COX-1 and a COX-2 inhibitor (i.e., a non-specific COX inhibitor). In a further embodiment, the COX inhibitor can be in any pharmaceutically acceptable form (e.g., salts, esters, prodrugs, etc.). The use of a COX inhibitor in conjunction with microneedles is described in U.S. patent application Ser. No. 12/325,919 which is incorporated by reference in its entirety.

Penetration Enhancers and Co-Solvents

In one embodiment, the pharmaceutical composition may comprise one or more penetration enhancing agent or co-solvent for transdermal or topical delivery. A penetration enhancer is an excipient that aids in the diffusion of the active through the stratum corneum. Many penetration enhancers also function as co-solvents which are thought to increase the thermodynamic activity or solubility of the cannabinoid in the composition and enhance drug delivery through the microneedle-created holes or pores. Penetration enhancers are also known as accelerants, adjuvants or sorption promoters. A suitable penetration enhancer for use in the pharmaceutical compositions and methods described herein should: (i) be highly potent, with a specific mechanism of action; (ii) exhibit a rapid onset upon administration; (iii) have a predictable duration of action; (iv) have only non-permanent or reversible effects on the skin; (v) be chemically stable; (vi) have no or minimal pharmacological effects; (vii) be physically and chemically compatible with other composition components; (viii) be odorless; (ix) be colorless; (x) be hypoallergenic; (xi) be non-irritating; (xii) be non-phototoxic; (xiii) be non-comedogenic; (xiv) have a solubility parameter approximating that of the skin (10.5 cal/cm3); (xv) be readily available; (xvi) be inexpensive; and (xvii) be able to formulated in pharmaceutical compositions for topical or transdermal delivery of an active pharmaceutical agent.

Several classes of chemical compounds, with various mechanisms of action, can be used as penetration enhancers. Set forth below are non-limiting examples of penetration enhancing agents, many of which are also suitable co-solvents. Sulfoxides, such as dimethylsulfoxide and decylmethylsulfoxide can be used as penetration enhancing agents. Dimethylsulfoxide enhances penetration in part by increasing lipid fluidity and promoting drug partitioning. In contrast, decylmethylsulfoxide enhances penetration by reacting with proteins in the skin that change the conformation of the proteins, which results in the creation of aqueous channels.

Another class of a penetration enhancers are alkanones, such as N-heptane, N-octane, N-nonane, N-decane, N-undecane, N-dodecane, N-tridecane, N-tetradecane and N-hexadecane. Alkanones are thought to enhance the penetration of an active agent by altering the stratum corneum. A further class of penetration enhancers are alkanol alcohols, such as ethanol, propanol, butanol, 2-butanol, pentanol, 2-pentanol, hexanol, octanol, nonanol, decanol and benzyl alcohol. Low molecular weight alkanol alcohols, i.e., those with 6 or less carbons, may enhance penetration in part by acting as solubilizing agents, while more hydrophobic alcohols may increase diffusion by extracting lipids from the stratum corneum. A further class of penetration enhancers are fatty alcohols, such as oleyl alcohol, caprylic alcohol, decyl alcohol, lauryl alcohol, 2-lauryl alcohol, myristyl alcohol, cetyl alcohol, stearyl alcohol, oleyl alcohol, linoleyl alcohol and linolenyl alcohol. Polyols, including propylene glycol, polyethylene glycol, ethylene glycol, diethylene glycol, triethylene glycol, dipropylene glycol, glycerol, propanediol, butanediol, pentanediol, hexanetriol, propylene glycol monolaurate and diethylene glycol monomethyl ether (transcutol), can also enhance penetration. Some polyols, such as propylene glycol, may function as a penetration enhancer by solvating alpha-kertin and occupying hydrogen bonding sites, thereby reducing the amount of active-tissue binding.

Another class of penetration enhancers are amides, including urea, dimethylacetamide, diethyltoluamide, dimethylformamide, dimethyloctamide, dimethyldecamide and biodegradable cyclic urea (e.g., 1-alkyl-4-imidazolin-2-one). Amides have various mechanisms of enhancing penetration. For example, some amides, such as urea increase the hydration of the stratum corneum, act as a keratolytic and create hydrophilic diffusion channels. In contrast, other amides, such as dimethylacetamide and dimethylformamide, increase the partition to keratin at low concentrations, while increasing lipid fluidity and disrupting lipid packaging at higher concentrations. Another class of penetration enhancing agents are pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-methyl-pyrrolidone, N-cyclohexylpyrrolidone, N-dimethylaminopropyl-pyrrolidone, N-cocoalkypyrrolidone and N-tallowalkypyrrolidone, as well as biodegradable pyrrolidone derivatives, including fatty acid esters of N-(2-hydroxyethyl)-2-pyrrolidone. In part, pyrrolidone derivatives enhance penetration through interactions with the keratin in the stratum corneum and lipids in the skin structure. An additional class of penetration enhancers are cyclic amides, including 1-dodecylazacycloheptane-2-one ("Azone"), 1-geranylazacycloheptan-2-one, 1-farnesylazacycloheptan-2-one, 1-geranylgeranylazacycloheptan-2-one, 1-(3,7-dimethyloctyl)-azacycloheptan-2-one, 1-(3,7,11-trimethyldodecyl)azacyclohaptan-2-one, 1-geranylazacyclohexane-2-one, 1-geranylazacyclopentan-2,5-dione and 1-farnesylazacyclopentan-2-one. Cyclic amides, such as Azone, enhance the penetration of active agents in part by affecting the stratum corneum's lipid structure, increasing partitioning and increasing membrane fluidity. Additional classes of penetration enhancers include diethanolamine, triethanolamine and hexamethylenlauramide and its derivatives.

Additional penetration enhancers include linear fatty acids, such as octanoic acid, linoleic acid, valeric acid, heptanoic acid, pelagonic acid, caproic acid, capric acid, lauric acid, myristric acid, stearic acid, oleic acid and caprylic acid. Linear fatty acids enhance penetration in part via selective perturbation of the intercellular lipid bilayers. In addition, some linear fatty acids, such as oleic acid, enhance penetration by decreasing the phase transition temperatures of the lipid, thereby increasing motional freedom or fluidity of the lipids. Branched fatty acids, including isovaleric acid, neopentanoic acid, neoheptanoic acid, nonanoic acid, trimethyl hexaonic acid, neodecanoic acid and isostearic acid, are a further class of penetration enhancers. An additional class of penetration enhancers are aliphatic fatty acid esters, such as ethyl oleate, isopropyl n-butyrate, isopropyl n-hexanoate, isopropyl n-decanoate, isopropyl myristate ("IPM"), isopropyl palmitate and octyldodecyl myristate. Aliphatic fatty acid esters enhance penetration by increasing diffusivity in the stratum corneum and/or the partition coefficient. In addition, certain aliphatic fatty acid esters, such as IPM, enhance penetration by directly acting on the stratum corneum and permeating into the liposome bilayers thereby increasing fluidity. Alkyl fatty acid esters, such as ethyl acetate, butyl acetate, methyl acetate, methyl valerate, methyl propionate, diethyl sebacate, ethyl oleate, butyl stearate and methyl laurate, can act as penetration enhancers. Alkyl fatty acid esters enhance penetration in part by increasing the lipid fluidity.

An additional class of penetration enhancers are anionic surfactants, including sodium laurate, sodium lauryl sulfate and sodium octyl sulfate. Anionic surfactants enhance penetration of active agents by altering the barrier function of the stratum corneum and allowing removal of water-soluble agents that normally act as plasticizers. A further class of penetration enhancers are cationic surfactants, such as cetyltrimethylammonium bromide, tetradecyltrimethylammonium, octyltrimethyl ammonium bromide, benzalkonium chloride, octadecyltrimethylammonium chloride, cetylpyridinium chloride, dodecyltrimethylammonium chloride and hexadecyltrimethylammonium chloride. Cationic surfactants enhance penetration by adsorbing at, and interacting with, interfaces of biological membranes, resulting in skin damage. A further class of penetration enhancers are zwitterionic surfactants, such as hexadecyl trimethyl ammoniopropane sulfonate, oleyl betaine, cocamidopropyl hydroxysultaine and cocamidopropyl betaine. Nonionic surfactants, including Polyxamer (231, 182, 184), Polysorbate (20, 60), Brij (30, 93, 96, 99), Span (20, 40, 60, 80, 85), Tween (20, 40, 60, 80), Myrj (45, 51, 52) and Miglyol 840, are yet another class of penetration enhancing agents. Nonionic surfactants enhance penetration in part by emulsifying the sebum and enhancing the thermodynamic activity or solubility of the active.

Another class of penetration enhancer increase the thermodynamic activity or solubility of the active, which include, but are not limited to, n-octanol, sodium oleate, D-limonene, monoolein, cineol, oleyl oleate, and isopropyl myristate.

Further penetration enhancers are bile salts, such as sodium cholate, sodium salts of taurocholic acid, glycolic acids and desoxycholic acids. Lecithin also has been found to have penetration enhancing characteristics. An additional class of penetration enhancers are terpenes, which include hydrocarbons, such as d-limonene, alpha-pinene and beta-carene; alcohols, such as, alpha-terpineol, terpinen-4-ol and carvol; ketones, such ascarvone, pulegone, piperitone and menthone; oxides, such as cyclohexene oxide, limonene oxide, alpha-pinene oxide, cyclopentene oxide and 1,8-cineole; and oils such as ylang ylang, anise, *chenopodium* and *eucalyptus*. Terpenes enhance penetration in part by disrupting the intercellular lipid bilayer to increase diffusivity of the active and opening polar pathways within and across the stratum corneum. Organic acids, such as salicylic acid and salicylates (including their methyl, ethyl and propyl glycol derivates), citric acid and succinic acid, are penetration enhancers. Another class of penetration enhancers are cyclodextrins, including 2-hydroxypropyl-beta-cyclodextrin and 2,6-dimethyl-beta-cyclodextrin. Cyclodextrins enhance the permeation of active agents by forming inclusion complexes with lipophilic actives and increasing their solubility in aqueous solutions.

Additional penetrations enhancers include, but are not limited to: alkyl-2-(N,N-disubstituted amino)-alkanoate ester (NexAct®); 2-(n-nonyl)-1,3-dioxolane (SEPA®); di(lower)alkyl esters of diacids (e.g., diisopropyl adipate); monoglyceride fatty acids (e.g., glyceryl monolaurate); tetrahydrofurfuryl alcohol; 2-(2-ethoxyethoxyl)ethanol; alkylaryl ethers of polyethylene oxide; polyethylene oxide monomethyl ethers; polyethylene oxide dimethyl ethers; acetoacetic ester; oleoyl macrogolglyceride; caprylocaproyl macrogolylyceride; polyoxyethylene 6 caprylic triglyceride; polyoxyethylene glyceride; PPG-5 ceteth-20; lauroyl macroglyceride oleic acid. Additional penetration enhancers suitable for use can also be found in U.S. patent application Ser. No. 10/032,163, which is incorporated by reference herein.

In one embodiment, the penetration enhancer would be (i) one or more co-solvents that increase the solubility of the cannabinoid (e.g., cannabidiol) or cannabinoid prodrug (e.g., a cannabidiol prodrug) but do not increase viscosity and/or (ii) compounds that increase blood flow to the microneedle treatment site (vasodilators).

Co-solvents include the penetration enhancers as described above. Further, co-solvent suitable for use include, but are not limited to, surfactants which can be found in U.S. Pat. No. 6,248,363, which is incorporated herein by reference in its entirety.

The penetration enhancing agent(s) and/or co-solvent(s) is/are present in an amount sufficient to provide the desired level of drug transport through the stratum corneum and epidermis or to increase the thermodynamic activity or solubility of the cannabinoid. Illustratively, one or more pharmaceutically acceptable penetration enhancer and/or co-solvent is present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

As a further illustration, one or more pharmaceutically acceptable penetration enhancer and/or co-solvent is present in a total amount by weight of about 1% to about 95%; about 5% to about 95%; about 10% to about 95%; about 15% to about 95%; about 20% to about 95%; about 25% to about 95%; about 30% to about 95%; about 35% to about 95%; about 40% to about 95%; about 45% to about 95%; about 50% to about 95%; about 55% to about 95%; about 60% to about 95%; about 65% to about 95%; about 70% to about 95%; about 75% to about 95%; about 80% to about 95%; about 85% to about 95%; about 90% to about 95%; about 1% to about 90%; about 5% to about 90%; about 10% to about 90%; about 15% to about 90%; about 20% to about 90%; about 25% to about 90%; about 30% to about 90%; about 35% to about 90%; about 40% to about 90%; about 45% to about 90%; about 50% to about 90%; about 55% to about 90%; about 60% to about 90%; about 65% to about 90%; about 70% to about 90%; about 75% to about 90%; about 80% to about 90%; about 85% to about 90%; about 1% to about 85%; about 5% to about 85%; about 10% to about 85%; about 15% to about 85%; about 20% to about 85%; about 25% to about 85%; about 30% to about 85%; about 35% to about 85%; about 40% to about 85%; about 45% to about 85%; about 50% to about 85%; about 55% to about 85%; about 60% to about 85%; about 65% to about 85%; about 70% to about 85%; about 75% to about 85%; about 80% to about 85%; about 1% to about 80%; about 5% to about 80%; about 10% to about 80%; about 15% to about 80%; about 20% to about 80%; about 25% to about 80%; about 30% to about 80%; about 35% to about 80%; about 40% to about 80%; about 45% to about 80%; about 50% to about 80%; about 55% to about 80%; about 60% to about 80%; about 65% to about 80%; about 70% to about 80%; about 75% to about 80%; about 1% to about 75%; about 5% to about 75%; about 10% to about 75%; about 15% to about 75%; about 20% to about 75%; about 25% to about 75%; about 30% to about 75%; about 35% to about 75%; about 40% to about 75%; about 45% to about 75%; about 50% to about 75%; about 55% to about 75%; about 60% to about 75%; about 65% to about 75%; about 70% to about 75%; about 1% to about 70%; about 5% to about 70%; about 10% to about 70%; about 15% to about 70%; about 20% to about 70%; about 25% to about 70%; about 30% to about 70%; about 35% to about 70%; about 40% to about 70%; about 45% to about 70%; about 50% to about 70%; about 55% to about 70%; about 60% to about 70%; about 65% to about 70%; about 1% to about 65%; about 5% to about 65%; about 10% to about 65%; about 15% to about 65%; about 20% to about 65%; about 25% to about 65%; about 30% to about 65%; about 35% to about 65%; about 40% to about 65%; about 45% to about 65%; about 50% to about 65%; about 55% to about 65%; about 60% to about 65%; about 1% to about 60%; about 5% to about 60%; about 10% to about 60%; about 15% to about 60%; about 20% to about 60%; about 25% to about 60%; about 30% to about 60%; about 35% to about 60%; about 40% to about 60%; about 45% to about 60%; about 50% to about 60%; about 55% to about 60%; about 1% to about 55%; about 5% to about 55%; about 10% to about 55%; about 15% to about 55%; about 20% to about 55%; about 25% to about 55%; about 30% to about 55%; about 35% to about 55%; about 40% to about 55%; about 45% to about 55%; about 50% to about 55%; about 1% to about 50%; about 5% to about 50%; about 10% to about 50%; about 15% to about 50%; about 20% to about 50%; about 25% to about 50%; about 30% to about 50%; about 35% to about 50%; about 40% to about 50%; about 45% to about 50%; about 1% to about 45%; about 5% to about 45%; about 10% to about 45%; about 15% to about 45%; about 20% to about 45%; about 25% to about 45%; about 30% to about 45%; about 35% to about 45%; about 40% to about 45%; about 1% to about 40%; about 5% to about 40%; about 10% to about 40%; about 15% to about 40%; about 20% to about 40%; about 25% to about 40%; about 30% to about 40%; about 35% to about 40%; about 1% to about 35%; about 5% to about 35%; about 10% to about 35%; about 15% to about 35%; about 20% to about 35%; about 25% to about 35%; about 30% to about 35%; about 1% to about 30%; about 5% to about 30%; about 10% to about 30%; about 15% to about 30%; about 20% to about 30%; about 25% to about 30%; about 1% to about 25%; about 5% to about 25%; about 10% to about 25%; about 15% to about 25%; about 20% to about 25%; about 1% to about 20%; about 5% to about 20%; about 10% to about 20%; about 15% to about 20%; about 1% to about 15%; about 5% to about 15%; or about 10% to about 15%; about 1% to about 10%; about 2% to about 10%; about 3% to about 10%; about 4% to about 10%; about 5% to about 10%; about 6% to about 10%; about 7% to about 10%; about 8% to about 10%; about 9% to about 10%; about 1% to about 9%; about 2% to about 9%; about 3% to about 9%; about 4% to about 9%; about 5% to about 9%; about 6% to about 9%; about 7% to about 9%; about 8% to about 9%; about 1% to about 8%; about 2% to about 8%; about 3% to about 8%; about 4% to about 8%; about 5% to about 8%; about 6% to about 8%; about 7% to about 8%; about 1% to about 7%; about 2% to about 7%; about 3% to about 7%; about 4% to about 7%; about 5% to about 7%; about 6% to about 7%; about 1% to about 6%; about 2% to about 6%; about 3% to about 6%; about 4% to about 6%; about 5% to about 6%; about 1% to about 5%; about 2% to about 5%; about 3% to about 5%; about 4% to about 5%; about 1% to about 4%; about 2% to about 4%; about 3% to about 4%; about 1% to about 3%; about 2% to about 3%; or about 1% to about 2%.

In an alternate embodiment, the weight percentage or weight percent range of penetration enhancer (i.e., co-solvent) is determined as a percentage of the total weight of the hydrogel.

Thickening or Gelling Agents and Related Excipients

In one embodiment, the pharmaceutical composition may comprise a thickening or gelling agent suitable for use in the compositions and methods described herein to increase the viscosity of the composition. Non-limiting examples of thickening agents (aka gelling agents), which may be used to create the composition or be present in the composition herein include neutralized anionic polymers or neutralized carbomers, such as polyacrylic acid (CARBOPOL® by Noveon, Inc., Cleveland, Ohio) (see information at http://www.nuven.com, incorporated by reference herein), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3. As used herein, a "neutralized carbomer" is a synthetic, high molecular weight polymer, composed primarily of a neutralized polyacrylic acid. Further, when a base is added to neutralize a carbomer solution, the viscosity of the solution increases. Also suitable are other known polymeric thickening agents, such as Pemulen® polymeric emulsifiers, Noveon® polycarbophils, and Klucel®. Additional thickening agents, enhancers and adjuvants may generally be found in Remington's The Science and Practice of Pharmacy as well as the Handbook of Pharmaceutical Excipients, Arthur H. Kibbe ed. 2000. Thickening agents or gelling agents are present in an amount sufficient to provide the desired rheological properties of the composition, which include having a sufficient viscosity for forming a gel or gel-like composition that can be applied to the skin of a mammal.

Illustratively, one or more pharmaceutically acceptable thickening agent or gelling agent is present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75%, about 10%, about 11%, about 11.5%, about 12%, about 12.5%, about 13%, about 13.5%, about 14%, about 14.5% or about 15%. As a further illustration, one or more pharmaceutically acceptable thickening or gelling agent is present in a total amount by weight of about 0.1% to about 15.0%; about 0.5% to about 5.0%; or about 1.0% to about 3.0%.

In another embodiment, the pharmaceutical composition contains an anionic polymer thickening agent precursor, such as a carbomer, which has been combined with a neutralizer in an amount sufficient to form a gel or gel-like composition with a viscosity greater than 1000 cps as measured by a Brookfield RV DVII+ Viscometer with spindle CPE-52, torque greater than 10% and the temperature maintained at 25° C.

In yet a further embodiment, the pharmaceutical composition contains an anionic polymer thickening agent precursor, such as a carbomer, which has been combined with a neutralizer selected from the group consisting of: sodium hydroxide, ammonium hydroxide, potassium hydroxide, arginine, aminomethyl propanol, tetrahydroxypropyl ethylenediamine, triethanolamine ("TEA"), tromethamine, PEG-15 cocamine, diisopropanolamine, and triisopropanolamine, or combinations thereof in an amount sufficient to neutralize the anionic polymer thickening agent precursor to form a gel or gel-like composition in the course of forming the composition. Suitable neutralizing agents and their use with selected anionic polymer thickening agent precursors are disclosed in "Neutralizing Carbopol® and Pemulen® Polymers in Aqueous and Hydroalcoholic Systems," Commercial Brochure TDS-237 (October 1998) by Noveon Inc. of Cleveland, Ohio, incorporated by reference herein.

In yet a further embodiment, the pharmaceutical composition contains an anionic polymer thickening agent precursor, such as a carbomer, which has been combined with a neutralizer which is an aqueous solution of sodium hydroxide, such as 0.01 N, 0.02 N, 0.025 N, 0.05 N, 0.075 N, 0.1 N sodium hydroxide, or 1.5 N sodium hydroxide, or 2.0 N sodium hydroxide or any other convenient strength aqueous solution in an amount sufficient to adequately neutralize the polyacrylic acid and form a gel or gel-like composition. In one embodiment, the composition was prepared using from about 1.0% to about 10.0% 0.025N sodium hydroxide. Accordingly, embodiments employing any percentage from about 1.0% to about 10.0% 0.025 N NaOH may be used, such as, e.g., 1.0%, 2.0%, 3.0%, 4.0%, 5.0%, 6.0%, 7.0%, 8.0%, 9.0% or 10% 0.025 N NaOH.

In an embodiment, the viscosity of a pharmaceutical composition described herein is about 1,000 cps to about 100,000 cps. Accordingly, the viscosity of the compositions described and disclosed herein may be any amount from about 1,000 cps to about 100,000 cps, such as, e.g., about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000, about 28,000, about 29,000, about 30,000, about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, about 50,000, about 51,000, about 52,000, about 53,000, about 54,000, about 55,000, about 56,000, about 57,000, about 58,000, about 59,000, about 60,000, about 61,000, about 62,000, about 63,000, about 64,000, about 65,000, about 66,000, about 67,000, about 68,000, about 69,000, about 70,000, about 71,000, about 72,000, about 73,000, about 74,000, about 75,000, about 76,000, about 77,000, about 78,000, about 79,000, about 80,000, about 81,000, about 82,000, about 83,000, about 84,000, about 85,000, about 86,000, about 87,000, about 88,000, about 89,000, about 90,000, about 91,000, about 92,000, about 93,000, about 94,000, about 95,000, about 96,000, about 97,000, about 98,000, about 99,000, about 100,000 cps.

In one embodiment, a neutralizing agent is optionally used to assist in forming a pharmaceutical composition. Suitable neutralizing agents include sodium hydroxide (e.g., as an aqueous mixture), potassium hydroxide (e.g., as an aqueous mixture), ammonium hydroxide (e.g., as an aqueous mixture), triethanolamine, tromethamine (2-amino 2-hydroxymethyl-1,3 propanediol), aminomethyl propanol (AMP), tetrahydroxypropyl ethylene diamine, diisopropanolamine, Ethomeen C-25 (Armac Industrial Division), Di-2 (ethylhexyl) amine (BASF-Wyandotte Corp., Intermediate Chemicals Division), triamylamine, Jeffamine D-1000 (Jefferson Chemical Co.), b-Dimethylaminopropionitrite (American Cyanamid Co.), Armeen CD (Armac Industrial Division), Alamine 7D (Henkel Corporation), dodecylamine and morpholine. The neutralizing agent is present in an amount sufficient to increase viscosity and form a gel or gel-like composition which is suitable for contact with the skin of a mammal. Illustratively, one or more pharmaceutically acceptable neutralizing agent is present in a total amount by weight of about 0.001%, about 0.0015%, about 0.01%, about 0.015%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%. As a further illustration, one or more pharmaceutically acceptable neutralizing agent is present in a total amount by weight of about 0.1% to about 7.0% or about 1.0% to about 5.0%.

In one embodiment, a solution of sodium hydroxide is used, such as, e.g., 0.01 N, 0.02 N, 0.025 N, 0.05 N, 0.075 N, 0.1 N sodium hydroxide solution, 0.2 N sodium hydroxide solution, 0.5 N sodium hydroxide solution, 1.0 N sodium hydroxide solution, 1.5 N sodium hydroxide solution, 2.0 N sodium hydroxide solution, 10.0 N sodium hydroxide solution, or any other suitable solution for providing a sufficient amount of the aqueous sodium hydroxide to form the desired gel or gel-like composition. In one embodiment, the pharmaceutically acceptable composition results from combining a gelling agent with a neutralizing agent such as about 1% to about 10% (wt/wt) 0.025 N sodium hydroxide, while in another embodiment about 0.1% to about 1% (wt/wt) 0.25 N sodium hydroxide is used. Of course, other suitable neutralizing agents can be used as can other concentrations and amounts of aqueous sodium hydroxide so long as there is a sufficient amount of OH⁻ ions to assist in the formation of a gel or gel-like composition.

Additional Excipients

The pharmaceutical compositions described herein optionally comprise one or more pharmaceutically acceptable wetting agents as excipients. Non-limiting examples of surfactants that can be used as wetting agents in compositions of the disclosure include quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10, and octoxynol 9; poloxamers (polyoxyethylene and polyoxypropylene block copolymers); polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether; polyoxyethylene fatty acid esters, for example polyoxyethylene (40) stearate; polyoxyethylene sorbitan esters, for example polysorbate 20 and polysorbate 80 (e.g., Tween™ 80 of ICI); propylene glycol fatty acid esters, for example propylene glycol laurate (e.g., Lauroglycol™ of Gattefossé); sodium lauryl sulfate, fatty acids and salts thereof, for example oleic acid, sodium oleate and triethanolamine oleate; glyceryl fatty acid esters, for example glyceryl monostearate; sorbitan esters (e.g., sorbitan monolaurate, sorbitan monooleate, sorbitan monopalmitate and sorbitan monostearate); tyloxapol and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75% or about 10%.

As used herein, a "solubility agent" or "solubilizing agent" is any excipient which is added to a pharmaceutical composition to increase the solubility of a solute.

The pharmaceutical compositions described herein optionally comprise one or more pharmaceutically acceptable lubricant, including an anti-adherent and/or a glidant.

Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; polyethylene glycol ("PEG") (e.g., Carbowax™ 4000 and Carbowax™ 6000); sodium oleate; sodium lauryl sulfate; and magnesium lauryl sulfate. Such lubricants, if present, constitute about 0.1% to about 10%, about 0.2% to about 8%, or about 0.25% to about 5%, of the total weight of the composition. Illustratively, one or more pharmaceutically acceptable lubricant is present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10%.

In another embodiment, the pharmaceutical compositions described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, althea *officinalis* extract, arachidyl alcohol, argobase EUC, butylene glycol, dicaprylate/dicaprate, *acacia*, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soyabean, octyl palmitate, caprylic/capric triglyceride and glyceryl cocoate. An emollient, if present, is present in the compositions described herein in an amount by weight of the composition of about 1% to about 30%, about 3% to about 25%, or about 5% to about 15%. Illustratively, one or more emollients are present in a total amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight.

In one embodiment, the pharmaceutical compositions described herein comprise an antioxidant. Illustrative antioxidants include citric acid, butylated hydroxytoluene (BHT), ascorbic acid, glutathione, retinol, α-tocopherol, μ-carotene, α-carotene, ubiquinone, butylated hydroxyanisole, ethylenediaminetetraacetic acid, selenium, zinc, lignan, uric acid, lipoic acid, and N-acetylcysteine. An antioxidant, if present, is present in the compositions described herein in the amount of about less than 1% by weight. Illustratively, one or more antioxidants are present in the total amount of about 0.025%, about 0.05%, about 0.075%, about 0.1%, about 0.125%, about 0.15%, about 0.175%, about 0.2%, about 0.225%, about 0.25%, about 0.275%, about 0.3%, 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1.0%, by weight. As a further illustration, one or more antioxidants are present in the total amount by weight of about 0.01% to about 1.0%; about 0.05% to about 0.5% or about 0.05% to about 0.2%.

In one embodiment, the pharmaceutical compositions described herein comprise an antimicrobial preservative. Illustrative anti-microbial preservatives include acids, including but not limited to, benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate or thimerosal. The anti-microbial preservative, if present, is present in an amount by weight of the composition of about 0.1% to about 5%, about 0.2% to about 3%, or about 0.3% to about 2%, for example about 0.2%, about 0.4%, about 0.6%, about 0.8%, about 1%, about 1.2%, about 1.4%, about 1.6%, about 1.8%, about 2%, about 2.2%, about 2.4%, about 2.6%, about 2.8%, about 3.0%, about 3.2%, about 3.4%, about 3.6%, about 3.8%, about 4%, about 4.2%, about 4.4%, about 4.6%, about 4.8%, or about 5%.

The pharmaceutical composition described herein optionally comprises one or more emulsifying agents. The term "emulsifying agent" refers to an agent capable of lowering surface tension between a non-polar and polar phase and includes self emulsifying agents. Suitable emulsifying agents can come from any class of pharmaceutically acceptable emulsifying agents including carbohydrates, proteins, high molecular weight alcohols, wetting agents, waxes and finely divided solids. The optional emulsifying agent, if present, is present in a composition in a total amount of about 1% to about 25%, about 1% to about 20%, or about 1% to about 15% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%.

In another embodiment, the pharmaceutical composition optionally comprises a water miscible solvent, such as propylene glycol. A suitable water miscible solvent refers to any solvent that is acceptable for use in a pharmaceutical composition and is miscible with water. If present, the water miscible solvent is present in a composition in a total amount of about 1% to about 95%, about 2% to about 75%, about 3% to about 50%, about 4% to about 40%, or about 5% to about 25% by weight of the composition. In a further embodiment, the water miscible solvent is present in a composition in an amount of about 1% to about 99%, by weight of the composition, for example about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%.

The pharmaceutical compositions described herein may optionally comprise one or more alcohols. In a further embodiment, the alcohol is a lower alcohol. As used herein, the term "lower alcohol," alone or in combination, means a straight-chain or branched-chain alcohol moiety containing one to about six carbon atoms. In one embodiment, the lower alcohol contains one to about four carbon atoms, and in another embodiment the lower alcohol contains two or three carbon atoms. Examples of such alcohol moieties include methanol, ethanol, ethanol USP (i.e., 95% v/v), n-propanol, isopropanol, n-butanol, isobutanol, sec-butanol, and tert-butanol. As used herein, the term "ethanol" refers to $C_2H_5OH$. It may be used as dehydrated alcohol USP, alcohol USP or in any common form including in combination with various amounts of water. If present, the alcohol is present in an amount sufficient to form a composition which is suitable for contact with a mammal. Illustratively, one or more pharmaceutically acceptable alcohol is present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98%. As a further illustration, one or more pharmaceutically acceptable alcohol is present in a total amount by weight of about 1% to about 98%; about 10% to about 95%; about 25% to about 75%; about 35% to about 70%; or about 40% to about 50%.

In a further embodiment, water is separately added to the pharmaceutical composition. The amount of water separately added to a pharmaceutical composition is exclusive of the amount of water independently present in the composition from any other component (e.g., alcohol, neutralizing agent). Water is present in an amount sufficient to form a composition which is suitable for administration to a mammal. Illustratively, water can be separately added by weight in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98%. As a further illustration, water can be separately added by weight in an amount of about 1% to about 98%; about 10% to about 70%; about 10% to about 40%; about 10% to about 30%; about 20% to about 30%; or about 25% to about 30%.

In a further embodiment, water is separately added to the pharmaceutical composition in a quantity or amount sufficient to achieve the desired weight of the pharmaceutical composition. In an additional embodiment, water is separately added in a quantity sufficient to obtain 100% weight of the composition.

In one embodiment, the pH of the pharmaceutical composition is suitable for administration to a mammal. In a further embodiment, the pH of the pharmaceutical composition is suitable for administration to the skin of a mammal. In additional embodiments, the pH of the pharmaceutical composition is suitable for buccal, sublingual, injection, rectal, vaginal, ocular, nasal or oral administration to a mammal. In one embodiment, the pH of the pharmaceutical composition is about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, about 9, about 9.1, about 9.2, about 9.3, about 9.4, about 9.5, about 9.6, about 9.7, about 9.8, about 9.9 or about 10. Illustratively, the pH of the pharmaceutical composition may be from about 3 to about 10, about 4 to about 8, about 4.5 to about 6.5, or about 5 to about 6.

Therapeutic Uses

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

It will be understood that a therapeutically and/or prophylactically effective amount of a drug for a subject is dependent inter alia on the body weight of the subject as well as other factors known to a person of ordinary skill in the art. A "subject" herein to which a therapeutic agent or composition thereof can be administered includes mammals, such as a human subject of either sex and of any age, and also includes any nonhuman animal, particularly a domestic or companion animal; illustratively a cat, dog or a horse as well as laboratory animals such as guinea pigs.

The terms "treat", "treated", "treating" and "treatment" are to be broadly understood as referring to any response to, or anticipation of, a medical condition in a mammal, particularly a human, and includes but is not limited to:
i. preventing the medical condition from occurring in a subject, which may or may not be predisposed to the condition, but has not yet been diagnosed with the condition and, accordingly, the treatment constitutes prophylactic treatment for the medical condition;
ii. inhibiting the medical condition, e.g., arresting, slowing or delaying the onset, development or progression of the medical condition; or
iii. relieving the medical condition, e.g., causing regression of the medical condition or reducing the symptoms of the medical condition.

In one embodiment, a therapeutically effective amount of a cannabinoid (e.g., cannabidiol) or a cannabinoid prodrug (e.g., a cannabidiol prodrug) is administered to treat alcohol use disorders and/or pancreatic illness, such as pancreatitis, acute pancreatitis, chronic pancreatitis or pancreatic cancer.

In other embodiments, a therapeutically effective amount of a cannabinoid (e.g., cannabidiol) or a cannabinoid prodrug (e.g., a cannabidiol prodrug) is administered to treat alcohol use disorders and/or a medical condition selected from the group consisting of: nausea, emesis, pain, wasting syndrome, HIV-wasting, chemotherapy induced nausea and vomiting, alcohol use disorders, dystonia, multiple sclerosis, inflammatory bowel disorders, arthritis, dermatitis, Rheumatoid arthritis, systemic lupus erythematosus, anti-inflammatory, anti-convulsant, anti-psychotic, antioxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritic, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, osteoarthritis, rheumatoid arthritis, synovitis, juvenile rheumatoid arthritis and inhibition of hair growth.

In a further embodiment, the cannabinoid gels, including hydrogels (which can be optionally incorporated into a patch system) and hydroalcoholic gels, described herein are used in conjunction with microneedles and are suitable for use for the relief of the pain of osteoarthritis of the joints, such as the hands, feet, ankles, wrists, shoulders, back, elbows and knees as well as the acute pain due to minor sprains, strains and contusions.

In one embodiment, the pharmaceutical composition containing a cannabinoid (e.g., cannabidiol) or a cannabinoid prodrug (e.g., a cannabidiol prodrug) is administered with the use of microneedles once daily to a subject in need thereof. In a further embodiment, the pharmaceutical composition containing a cannabinoid, such as cannabidiol, or a cannabinoid prodrug, such as a cannabidiol prodrug, is administered with the use of microneedles twice daily to a subject in need thereof. In a further embodiment, the pharmaceutical composition is administered with the use of microneedles more than twice daily, such as three, four, five, six, seven or eight times daily or once, twice, three, four, five or six times per week. In a further embodiment, the pharmaceutical composition is administered weekly, every two weeks, every three weeks, every four weeks, every five weeks, or every six weeks.

Pharmaceutical Dosage Forms

The pharmaceutical compositions described herein are used in a "pharmacologically effective amount." A "pharmacologically effective amount" is the amount of the active pharmaceutical agent in the composition which is sufficient to deliver a therapeutic amount of the active agent during the dosing interval in which the pharmaceutical composition is administered.

In one embodiment, the amount of the pharmaceutical composition (e.g., the total weight of the hydrogel) administered to deliver a therapeutically effective amount of the cannabinoid, such as cannabidiol or cannabidiol prodrug, is about 0.01 g, about 0.05 g, about 0.1 g, about 0.2 g, about 0.3 g, about 0.4 g, about 0.5 g, about 0.6 g, about 0.7 g, about 0.8 g, about 0.9 g, about 1 g, about 1.1 g, about 1.2 g, about 1.3 g, about 1.4 g, about 1.5 g, about 1.6 g, about 1.7 g, about 1.8 g, about 1.9 g, about 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5 g, about 3.6 g, about 3.7 g, about 3.8 g, about 3.9 g, about 4 g, about 4.1 g, about 4.2 g, about 4.3 g, about 4.4 g, about 4.5 g, about 4.6 g, about 4.7 g, about 4.8 g, about 4.9 g, about 5 g, about 5.1 g, about 5.2 g, about 5.3 g, about 5.4 g, about 5.5 g, about 5.6 g, about 5.7 g, about 5.8 g, about 5.9 g, about 6 g, about 6.1 g, about 6.2 g, about 6.3 g, about 6.4 g, about 6.5 g, about 6.6 g, about 6.7 g, about 6.8 g, about 6.9 g, about 7 g, about 7.1 g, about 7.2 g, about 7.3 g, about 7.4 g, about 7.5 g, about 7.6 g, about 7.7 g, about 7.8 g, about 7.9 g, about 8 g, about 8.1 g, about 8.2 g, about 8.3 g, about 8.4 g, about 8.5 g, about 8.6 g, about 8.7 g, about 8.8 g, about 8.9 g, about 9 g, about 9.1 g, about 9.2 g, about 9.3 g, about 9.4 g, about 9.5 g, about 9.6 g, about 9.7 g, about 9.8 g, about 9.9 g or about 10 g.

Illustratively, the amount of the pharmaceutical composition administered to deliver a therapeutically effective amount of a cannabinoid (e.g., cannabidiol) or a cannabinoid prodrug (e.g., a cannabidiol prodrug) is about 0.01 g to about 10 g, about 0.01 g to about 6 g, about 0.01 g to about 4 g, or about 0.01 g to about 2 g.

In one embodiment, a single dosage unit of any pharmaceutical composition described herein comprises a therapeutically effective amount or a therapeutically and/or prophylactically effective amount of a cannabinoid, such as cannabidiol or a prodrug of cannabidiol.

In one embodiment, the pharmaceutical compositions described herein are suitable for transdermal administration, in conjunction with a microneedle array, comprising the microneedle transdermal drug delivery system. In another embodiment, microneedle transdermal drug delivery systems are adapted for administration in and/or around the abdomen, back, chest, legs, arms, scalp or other suitable skin surface and may include compositions in which the cannabinoid or cannabinoid prodrug is administered in patches (which can optionally contain a hydrogel), ointments, creams, suspensions, lotions, pastes, gels, hydrogels (which can be optionally incorporated into a patch), sprays, foams or oils. In another embodiment, the pharmaceutical compositions described herein comprise a cannabinoid, such as cannabidiol or a cannabinoid prodrug, in a pharmaceutical gel or gel-like composition, which are transdermally administrable, in conjunction with a microneedle array, as part of a microneedle transdermal drug delivery system.

In one embodiment, the pharmaceutical compositions described herein are suitable for topical administration, in conjunction with a microneedle array, comprising the microneedle topical drug delivery system. In another embodiment, microneedle topical drug delivery systems are adapted for administration in and/or around the abdomen, back, chest, legs, arms, scalp or other suitable skin surface and may include compositions in which the a cannabinoid, such as cannabidiol or prodrug of cannabidiol, is administered in patches (which can optionally contain a hydrogel), ointments, creams, suspensions, lotions, pastes, gels, hydrogels (which can be optionally incorporated into a patch), sprays, foams or oils. In another embodiment, the pharmaceutical compositions described herein comprise a cannabinoid, such as cannabidiol or a prodrug of cannabidiol, in a pharmaceutical gel or gel-like composition which are transdermally administrable, in conjunction with a microneedle array, as part of a microneedle topical drug delivery system.

In one embodiment, the pharmaceutical compositions described herein are administered via a membrane-modulated transdermal delivery system used in conjunction with a microneedle array. Together, the pharmaceutical composition and the microneedle array comprise a "microneedle drug delivery system." In one embodiment of the microneedle drug delivery system, this membrane-modulated transdermal delivery system comprises a reservoir containing a cannabinoid (e.g., cannabidiol) or a cannabinoid prodrug (e.g., a cannabidiol prodrug) to be transdermally administered to the patient can be encapsulated in a shallow compartment molded from a drug impermeable backing and a rate controlling polymeric membrane through which the cannabinoid passes in a controlled manner in conjunction with a microneedle array. In another embodiment, the external surface of the membrane has a thin layer of a drug-compatible, hypoallergenic adhesive polymer (e.g., silicone or polyacrylate adhesive) which is applied to achieve intimate contact with the skin of a mammal.

In another embodiment, the pharmaceutical compositions described herein are administered via an adhesive-diffusion controlled transdermal system used in conjunction with a microneedle array. Together, the pharmaceutical composition and the microneedle array comprise a "microneedle drug delivery system." In these embodiments, the pharmaceutical composition acts as a reservoir by directly dispersing a cannabinoid (e.g., cannabidiol) or a cannabinoid prodrug (e.g., a cannabidiol prodrug) to be delivered in an adhesive polymer and then spreading the medicated adhesive onto a flat sheet of drug-impermeable backing membrane to form a thin active pharmaceutical agent reservoir layer. Optionally, additional layers of non-medicated rate controlling adhesive polymer with a constant thickness are placed on top of the drug reservoir layer to produce an adhesive diffusion-controlled drug-delivery system. The resulting adhesive-diffusion controlled transdermal system is then applied to the desired area of the skin of a mammal in conjunction with a microneedle array.

In a further embodiment, the pharmaceutical compositions described herein are administered via matrix dispersion-type systems in conjunction with microneedle arrays. Together, the pharmaceutical composition and the microneedle array comprise a "microneedle drug delivery system." The dispersion-type system comprises a reservoir containing a cannabinoid (e.g., cannabidiol) or a cannabinoid prodrug (e.g., a cannabidiol prodrug) which can be formed by homogeneously dispersing the cannabinoid or cannabinoid prodrug in a hydrophilic or lipophilic polymer matrix. The medicated polymer is then molded into a medicated disc with a defined surface area and controlled thickness which is glued onto an occlusive baseplate in a compartment fabricated from a drug-impermeable backing. The adhesive polymer is spread along the circumference to form a strip of adhesive rim around the medicated disc. The resulting dispersion-type system is then applied to the desired area of the skin in conjunction with a microneedle array.

In still another embodiment, the pharmaceutical compositions described herein are administered via microreservoir systems in conjunction with microneedle arrays. Together, the pharmaceutical composition and the microneedle array comprise a "microneedle drug delivery system." The microreservoir system comprises a drug reservoir which is formed by first suspending particles of a cannabinoid (e.g., cannabidiol) or a cannabinoid prodrug (e.g., a cannabidiol prodrug) in an aqueous solution of water-soluble polymer and then dispersing it homogeneously in a lipophilic polymer by high-shear mechanical force to form a large number of unleachable, microscopic spheres reservoirs of the cannabinoid or cannabinoid prodrug. This unstable dispersion is quickly stabilized by immediately cross-linking the polymer which produces a medicated polymer disc with a constant surface area and fixed thickness. A microreservoir system is produced in which the medicated disc is positioned at the center and surrounded by an adhesive rim. The resulting microreservoir system is then applied to the desired area of the skin in conjunction with a microneedle array.

In another embodiment, the pharmaceutical compositions described herein are administered via one monolithic layer, comprising a cannabinoid (e.g., cannabidiol) or a cannabinoid prodrug (e.g., a cannabidiol prodrug) and an adhesive, in conjunction with a microneedle array. Together, the pharmaceutical composition and the microneedle array comprise a "microneedle drug delivery system." The cannabinoid can be mixed with an adhesive (e.g., silicone type, available from Dow Corning and other manufacturers) in a solvent (e.g., methylene chloride or ethyl acetate). This resulting mixture would then be extruded onto a polyester backing film to a uniform thickness of about 100 microns or greater with a precision wet-film applicator. The solvent is allowed to evaporate in a drying oven and the resulting "patch" is trimmed to the appropriate size. Various patch compositions will be made until the desired steady-state flux rate and adhesive properties are obtained. Different adhesives can be tried, as well as varying the amount of adhesive in the composition (Nalluri, Milligan et al. 2005). Suitable results have been obtained by making monolithic patches with DURO-TAK 387-2051, which is an acrylate-vinyl acetate non-curing pressure sensitive adhesive from the National Starch Chemical Company. Different solvents (e.g., isopropyl myristate, propylene glycol) can optionally be incorporated into the composition in an attempt to optimize the delivery rate of the active pharmaceutical agent. In a further embodiment, the pharmaceutical compositions described herein are administered via the reservoir system in conjunction with a microneedle array. Together, the pharmaceutical composition and the microneedle array comprise a "microneedle drug delivery system." The cannabinoid (e.g., cannabidiol) or a cannabinoid prodrug (e.g., a cannabidiol prodrug) and any excipient(s) could be formulated into a gel and sealed between a release layer and an impermeable backing material such as polyester or other suitable material known to a person of skill in the art. Ethyl vinyl acetate membranes with acrylic adhesives have been found to be suitable. In each of the foregoing embodiments, the patch would then be applied to the desired area of the skin in conjunction with a microneedle array.

Adhesive patch compositions can be prepared containing different loadings of a pharmaceutical composition comprising a cannabinoid (e.g., cannabidiol) or a cannabinoid prodrug (e.g., a cannabidiol prodrug) to be delivered transdermally by using DURO-TAK adhesives (National Starch and Chemical Company, USA). Appropriate amounts of adhesive and drug can be sonicated for ten minutes, cast onto the release liner (9742 Scotchpak, 3M, St. Paul, Minn.) with a wet film applicator (Paul N. Gardner Company, Inc., Pompano Beach, Fla.) set at a 40 mil thickness, and kept at room temperature for one hour and then at 70° C. in an oven for ten minutes (to remove any residual solvent). The patches would then be covered with backing membrane (CoTran 9722, 3M, St. Paul, Minn.), will be cut into appropriate sizes, and then can be stored in a desiccator for further study. The resulting patches would then be applied to the desired area of the skin in conjunction with a microneedle array.

In further embodiments, a combination of two or more types of adhesives may be used, such as DURO-TAK 900A and a silicon adhesive such as one produced by DOW, in a ratio from 1:99 to 99:1 in order to optimize release rates and drug solubility.

In further embodiments, additional adhesives which are suitable for preparing patch transdermal delivery systems, such as patches include polyisobutylenes, acrylates, silicone and combinations of the foregoing, may be used. Additional adhesives can be found in U.S. patent application Ser. No. 11/860,432, published as US 2008/0076789 on Mar. 27, 2008.

In another illustrative embodiment, the transdermal patch incorporating a cannabinoid (e.g., cannabidiol) or a cannabinoid prodrug (e.g., a cannabidiol prodrug) is applied to the desired area of the skin in conjunction with a microneedle array and is capable of controlling the release of the active pharmaceutical agent such that transdermal delivery of the active pharmaceutical agent to the subject is substantially uniform and sustained over a period of about 1 hour, about 2 hours, about 3 hours, about 4 hours, about 6 hours, about 12 hours, about 24 hours, about 48 hours, about 72 hours, about 96 hours, about 5 days, about 6 days or about 7 days. In an alternative embodiment, the patch further incorporates a penetration enhancer and/or a COX inhibitor and optionally includes a hydrogel. Such a transdermal patch, which can be used in the practice of the methods described herein, can take the form of an occlusive body. In practice, the occlusive body, which includes the pharmaceutical composition comprising a COX inhibitor, a penetration enhancer and a cannabinoid (e.g., cannabidiol) or a cannabinoid prodrug (e.g., a cannabidiol prodrug) is applied to the desired area of the skin in conjunction with a microneedle array to transdermally or topically deliver the active pharmaceutical agent.

In another embodiment, the pharmaceutical compositions described herein are administered via a hydrogel in conjunction with microneedle arrays. Together, the pharmaceutical composition and the microneedle array comprise a "microneedle drug delivery system." In one embodiment, the hydrogel is trimmed to an appropriate size and shape, and allowed to equilibrate with a cannabinoid- or cannabinoid prodrug-containing loading solution. In one embodiment, the loading solution comprises a cannabinoid or a cannabinoid prodrug (e.g. cannabidiol or a prodrug of cannabidiol), polyethylene glycol, ethanol, benzyl alcohol and water. In another embodiment, the hydrogel comprises a cannabinoid (e.g., cannabidiol) or a cannabinoid prodrug (e.g., a cannabidiol prodrug). The hydrogel would then be applied to the desired area of the skin in conjunction with a microneedle array. Optionally, the hydrogel can be incorporated into a patch which can be applied to the desired area of the skin in conjunction with a microneedle array. Examples of suitable hydrogels include AquaSite® (Derma Science, Inc., Princeton, N.J.), AquaFlo® Hydrogel Wound Dressing (The Kendall Company, Mansfield, Mass.), Aqua- Clear® (Hartmann-Conco Inc., Rock Hill, S.C.) and 3M™ Tegaderm™ Hydrocolloid Dressing (3M, St. Paul, Minn.).

A "hydrogel" (aka aquagel) is a hydrocolloidal polymer gel comprising a hydrophilic natural or synthetic gel-forming polymer dispersed in water. Hydrophilic polymers include natural gums, such as gum karaya, guar gum, locust bean gum, gum arabic, gum tragacanth, agarm alginic acid, carrageenan or other polysaccharides; synthetically modified polysaccharides, such as carboxymethyl cellulose, carboxypropyl cellulose and maltodextrin; and synthetic polymers, such as polyacrylamide, polyacrylic acid, polyquaternary amine and polysulfonate. Hydrogels are highly absorbent, flexible, and similar to natural tissue.

One embodiment described herein employs a packet having a polyethylene liner compatible with a pharmaceutical composition comprising a cannabinoid, such as cannabidiol or a prodrug of cannabidiol. The packet may hold a unit dose or multiple dose.

EXAMPLES

Example 1

A pharmaceutical composition, comprising cannabidiol or a cannabidiol prodrug and optionally a penetration enhancer and/or COX inhibitor, is administered via a membrane-modulated transdermal delivery system in conjunction with the microneedle array. Together, the pharmaceutical composition and the microneedle array comprise a "microneedle drug delivery system." The composition reservoir is encapsulated in a shallow compartment molded from a drug impermeable backing and a rate controlling polymeric membrane through which the cannabidiol or cannabidiol prodrug passes in a controlled manner. The external surface of the membrane has a thin layer of a drug-compatible, hypoallergenic adhesive polymer (e.g., silicone, polyisobutylene or polyacrylate adhesive) which is applied to achieve intimate contact of the transdermal system with the skin of a mammal in conjunction with a microneedle array to treat a disease or condition responsive to cannabinoid therapy, such as acute or chronic pancreatitis, pancreatic cancer, pain, inflammation or alcohol use disorders.

Example 2

A pharmaceutical composition, comprising cannabidiol or a cannabidiol prodrug and optionally a penetration enhancer and/or COX inhibitor, is administered via an adhesive-diffusion controlled transdermal system in conjunction with the microneedle array. Together, the pharmaceutical composition and the microneedle array comprise a "microneedle drug delivery system." The pharmaceutical composition is formulated to act as an adhesive polymer containing cannabidiol or a cannabidiol prodrug. The medicated adhesive composition is spread onto a flat sheet of drug-impermeable backing membrane and forms a thin active pharmaceutical agent reservoir layer. The pharmaceutical composition is then administered to the skin of a mammal in conjunction with a microneedle array to treat a disease or condition responsive to cannabinoid therapy, such as acute or chronic pancreatitis, pancreatic cancer, pain, inflammation or alcohol use disorders.

Example 3

A pharmaceutical composition, comprising cannabidiol or a cannabidiol prodrug and optionally a penetration enhancer and/or COX inhibitor, is administered via an adhesive-diffusion controlled transdermal system in conjunction with the microneedle array. Together, the pharmaceutical composition and the microneedle array comprise a "microneedle drug delivery system." At least one layer of a non-medicated, rate-controlling adhesive polymer, with a constant thickness, is placed on top of the pharmaceutical composition to produce an adhesive diffusion-controlled drug-delivery system. The resulting adhesive-diffusion controlled transdermal system is then applied to the desired area of the skin of a mammal in conjunction with a microneedle array to treat a disease or condition responsive to cannabinoid therapy, such as acute or chronic pancreatitis, pancreatic cancer, pain, inflammation or alcohol use disorders.

Example 4

A pharmaceutical composition, comprising cannabidiol or a cannabidiol prodrug and optionally a penetration enhancer and/or COX inhibitor, is administered via matrix dispersion-type system in conjunction with the microneedle array. Together, the pharmaceutical composition and the microneedle array comprise a "microneedle drug delivery system." The composition is formed by homogeneously dispersing cannabidiol or a cannabidiol prodrug in a polymer matrix. The medicated polymer composition then is molded into a disc with a defined surface area and controlled thickness. The disc then is glued onto an occlusive baseplate in a compartment fabricated from a drug-impermeable backing. An adhesive polymer is spread along the circumference of the composition disc to form a strip of adhesive rim around disc. The resulting dispersion-type transdermal system is then applied to the desired area of the skin of a mammal in conjunction with a microneedle array to treat a disease or condition responsive to cannabinoid therapy, such as acute or chronic pancreatitis, pancreatic cancer, pain, inflammation or alcohol use disorders.

Example 5

A pharmaceutical composition, comprising cannabidiol or a cannabidiol prodrug and optionally a penetration enhancer and/or COX inhibitor, is administered via microreservoir systems in conjunction with the microneedle array. Together, the pharmaceutical composition and the microneedle array comprise a "microneedle drug delivery system." The composition reservoir is formed by first suspending cannabidiol or cannabidiol prodrug particles in an aqueous solution of water-soluble polymer. The suspension is then dispersed homogeneously in a lipophilic polymer by high-shear mechanical force to form a large number of unleachable, microscopic spheres reservoirs. This unstable dispersion is quickly stabilized by immediately cross-linking the polymer which produces a medicated polymer disc with a constant surface area and fixed thickness. The medicated disc is positioned at the center and surrounded by an adhesive rim. The resulting microreservoir transdermal system is then administered to the desired area of the skin of a mammal in conjunction with a microneedle array for the treatment of a disease or condition responsive to cannabinoid therapy, such as acute or chronic pancreatitis, pancreatic cancer, pain, inflammation or alcohol use disorders.

Example 6

A pharmaceutical composition, comprising cannabidiol or a cannabidiol prodrug and optionally a penetration enhancer and/or COX inhibitor, is administered via one monolithic layer and an adhesive, in conjunction with the microneedle array. Together, the pharmaceutical composition and the microneedle array comprise a "microneedle drug delivery system." The composition is mixed with an adhesive (e.g., silicone type, available from Dow Corning and other manufacturers) in a solvent (e.g., methylene chloride or ethyl acetate). This resulting mixture is then extruded onto a polyester backing film to a uniform thickness of about 100 microns or greater with a precision wet-film applicator. The solvent is allowed to evaporate in a drying oven and the resulting "patch" is trimmed to the appropriate size. The pharmaceutical composition is then administered to the skin of mammal in conjunction with a microneedle array to treat a disease or condition responsive to cannabinoid therapy, such as pancreatitis, pancreatic cancer, pain, inflammation or alcohol use disorders.

Example 7

A pharmaceutical composition, comprising cannabidiol or a cannabidiol prodrug and optionally a penetration enhancer and/or COX inhibitor, is administered as a reservoir patch in conjunction with the microneedle array. Together, the pharmaceutical composition and the microneedle array comprise a "microneedle drug delivery system." The composition is a gel that is sealed between a release layer and an impermeable backing material, such as polyester. The patch is then administered to the desired area of the skin of a mammal in conjunction with a microneedle array to treat a disease or condition responsive to cannabinoid therapy, such as acute or chronic pancreatitis, pancreatic cancer, pain, inflammation or alcohol use disorders.

Example 8

A pharmaceutical composition, comprising cannabidiol or a cannabidiol prodrug and optionally a penetration enhancer and/or COX inhibitor in a gel composition, is administered in conjunction with the microneedle array. Together, the pharmaceutical composition and the microneedle array comprise a "microneedle drug delivery system." The gel composition is prepared and stored in a packet having a polyethylene liner compatible with the pharmaceutical composition. The packet may hold a unit dose or multiple doses. The composition is administered by opening the packet, removing a dose of the composition, and applying it to the skin of a mammal in conjunction with a microneedle array to treat a disease or condition responsive to cannabinoid therapy, such as acute or chronic pancreatitis, pancreatic cancer, pain, inflammation or alcohol use disorders. In one embodiment, the treated skin is occluded with an occlusive dressing for long-term wear. In another embodiment, the treated skin is occluded with an occlusive dressing for short-term wear.

Example 9

A pharmaceutical composition, comprising cannabidiol or a cannabidiol prodrug and optionally a penetration enhancer and/or COX inhibitor in a gel composition, is administered in conjunction with a microneedle array. Together, the pharmaceutical composition and the microneedle array comprise a "microneedle drug delivery system." The gel composition is prepared and stored in rigid multi-dose container (for example, with a hand pump) having a larger foil packet insert. The larger packet comprises a polyethylene liner. The composition is then administered to the skin of the mammal in conjunction with a microneedle array to treat a disease or condition responsive to cannabinoid therapy, such as acute or chronic pancreatitis, pancreatic cancer, pain, inflammation or alcohol use disorders. In one embodiment, the treated skin is occluded with an occlusive dressing for long-term wear. In another embodiment, the treated skin is occluded with an occlusive dressing for short-term wear.

Example 10

A pharmaceutical composition, comprising cannabidiol or a cannabidiol prodrug and optionally a penetration enhancer and/or COX inhibitor in a hydrogel, is administered in conjunction with a microneedle array. Together, the pharmaceutical composition and the microneedle array comprise a "microneedle drug delivery system." The hydrogel comprising the cannabidiol or cannabidiol prodrug is applied to the desired area of the skin of the mammal in conjunction with a microneedle array to treat a disease or condition responsive to cannabinoid therapy, such as acute or chronic pancreatitis, pancreatic cancer, pain, inflammation or alcohol use disorders. In one embodiment, the treated skin is occluded with an occlusive dressing for long-term wear. In another embodiment, the treated skin is occluded with an occlusive dressing for short-term wear.

Example 11

Solution Permeation Results for a Cannabidiol Prodrug with Microneedles a) Synthesis of a Cannabidiol Prodrug (ALL00179)

Anhydrous betaine was converted to the acyl chloride using thionyl chloride. Cannabidiol (CBD) (273.23 mg, 0.00087 mol), triethylamine (263.6 mg, 0.00261 mol) and the converted betaine (374.2 mg, 0.00218 mol) were combined in 5 mL dry dichloromethane under argon. The reaction mixture was stirred at room temperature (RT) for two hours. Additional triethylamine (175.7 mg, 0.00174 mol) and betaine acyl chloride (149.7 mg, 0.00087 mol) were added to the reaction mixture while flushing with argon. The mixture was stirred for another hour at RT.

The reaction mixture was transferred to a separatory funnel containing 50 mL each of acetonitrile and water saturated with sodium chloride. The contents of the flask were shaken well and the layers allowed to separate. The acetonitrile layer was collected and most of the residual water was removed by stirring for one hour with anhydrous sodium sulfate. The sodium sulfate was removed by filtration and the acetonitrile transferred to a round bottom flask. The volume of acetonitrile was reduced by rotary evaporation until a small amount of water remained. The remaining water was transferred to an Erlenmeyer flask containing acetonitrile and again the residual water was removed with anhydrous sodium sulfate. The mixture was again filtered and the filtrate was collected in a round bottom flask. The acetonitrile was completely removed by rotary evaporation and high vacuum. The tan powder obtained was transferred to a vial, sealed and stored at −20° C.

ALL00179 was analyzed by LC/MS using electrospray in the positive ion mode. The mass spectrum of the compound was observed as follows: m/z=513.426 ($M^+$, no chloride counter ions, 6% abundance), m/z=414.358 ($M^+$—one betaine chain, no chloride counter ion, 8%), m/z=257.357 (90%), m/z=223.363, (100%).

For ALL00179, the $^1$H NMR (400 MHz, CD3OD) was as follows: $\delta$ =7.04 (2H, s, ArH); 5.16 (1H, s, H-2); 4.70-4.84 (4H, m, $CH_2CO_2$); 3.56-3.65 (1H, m, H-3); 3.42 (18H, s, $N(CH_3)_3$); 2.60-2.70 (1H, m); 2.60-2.66 (2H, m, benzylic $CH_2$); 2.32-2.44 (1H, m); 2.04-2.13 (1H, m); 1.79-1.88 (2H, m); 1.70 (3H, br s, 7-Me); 1.59-1.68 (2H, m); 1.56 (3H, s, 10-Me); 0.90 (3H, t, J=7.0, $CH_2C\underline{H}_3$).

Illustratively, the molecular structure of ALL00179 as shown below:

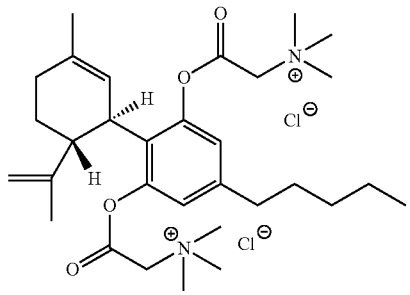 [SMILES: C=C(C)[C@@H]1CCC(C)=C[C@H]1c1c(OC(=O)C[N+](C)(C)C)cc(CCCCC)cc1OC(=O)C[N+](C)(C)C ; [Cl-] ; [Cl-]]

b) Stability of the Cannabidiol Prodrug

Stability of the prodrug in human plasma was performed to monitor the conversion of ALL00179 to the mono-substituted form, ALL00180, and CBD. The molecular structure of ALL00180 and CBD are shown below:

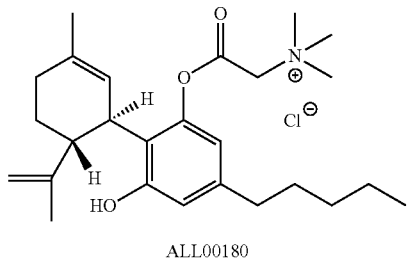

ALL00180

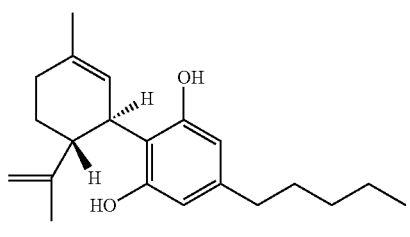

CBD

TABLE 1

Cannabidiol and Cannabidiol Prodrugs Molecular Weight

| Compound | Molecular weight |
| --- | --- |
| Cannabidiol | 314.4 |
| ALL00179 | 585.65 |
| ALL00180 | 450.05 |

ALL00179 was placed in 100% ddH$_2$O donor solution to check chemical stability. The initial purity of ALL00179 was 94.7% ALL00179, 5.3% ALL00180, and 0% CBD. After 72 hr in ddH$_2$O at RT, the purity level was determined to be 86.8% ALL00179, 13.2% ALL00180 and 0% CBD.

TABLE 2

Stability of ALL00179 in Human Plasma
Percent Prodrug and CBD at time (min)

| Prodrug | 0* | 5 | 10 | 20 | 30 | 60 | 120 |
| --- | --- | --- | --- | --- | --- | --- | --- |
| CBD | 4.7 | 30.2 | 55.1 | 77.1 | 89.4 | 97.6 | 100 |
| ALL00179 | 9.2 | 3.0 | 0.0 | 0.0 | 0.0 | 0.0 | 0.0 |
| ALL00180 | 86.1 | 66.8 | 44.9 | 22.9 | 10.6 | 2.4 | 0.0 |

*Time point 0 required approximately 1 minute of mixing and withdrawal time after addition of ALL00179 to the human plasma and before the sample was placed into acetonitrile for extraction and analysis. The spiking solution was shown to contain at least 88% ALL00179. ALL00179 rapidly hydrolyzed to the mono-substituted prodrug form, ALL0180, which further hydrolyzed to CBD.

c) Diffusion Study

The purpose of the diffusion study was to determine whether microneedle (MN) treated skin would allow the rapid permeation of a water-soluble prodrug of CBD (ALL00179) compared to CBD.

Briefly, full thickness Yucatan pig (YP) skin was used to perform the microneedle studies. The average thickness of the YP skin was approximately 1.0±0.1 mm. A PermeGear flow-through (In-Line, Hellertown, Pa.) diffusion cell system was used for the skin permeation studies. One hundred microneedle insertions were made into the skin before mounting in the flow-through diffusion cell by treating the skin 20 times with an array containing 5 microneedles. Each cell was charged with 250 μl of either 318 mM CBD (n=4) or ALL00179 (n=5) and occluded with rubber stoppers. Ten percent ethanol in water was used as a receiver solution. Samples were collected at six-hour intervals for a total of 48 hours. (See FIG. 1 for the permeation profile.)

TABLE 3

HPLC Conditions of CBD and CBD Prodrugs, ALL00179 and ALL00180, for Microneedle in vitro Diffusion Studies and Plasma Stability Studies.

| | |
| --- | --- |
| Column | Brownlee ® C$_{18}$ reversed-phase Spheri VL, 5 μm, (4.6 × 220 mm) column with a Brownlee ® C$_{18}$ reversed-phase, 5 μm, (3.2 × 150 mm) guard column |
| Mobile phase | 85:15 acetonitrile:0.05% trifluoroacetic acid, pH 3 with triethylamine, with 5% acetonitrile, |
| Flow rate | 1.5 mL/min |
| Wavelength | 210 nm |
| Injection volume | 100 μL (diffusion samples and respective standards) 20 μL (skin samples, donor samples, and respective standards) |
| Run time | 9.5 min |
| Retention times | Cannabidiol (CBD) = 3.6 min ALL00179 = 8.2 min ALL00180 = 5.6 min |

TABLE 4

Permeation Data for Cannabidiol (n = 4) and Total CBD from ALL00179 (n = 5) in a 100% ddH$_2$O Donor Solution through Yucatan Pig Skin after Microneedle Treatment.

| Compound | 48 h skin conc (μmol/g) | 48 h cumulative amt (nmol) | Flux (nmol/cm$^2$/h) | Lag time (h) |
|---|---|---|---|---|
| Cannabidiol (CBD) (MN treated) | 0.12 ± 0.09 | 0.0 ± 0.0 | 0.0 ± 0.0 | ND |
| Total CBD* from ALL00179 (MN treated) | 2.4 ± 2.8 | 3110.7 ± 686.0 | 63.2 ± 11.4 | 2.5 ± 3.0 |

*total CBD = total cannabidiol equivalents delivered in the form of cannabidiol and/or prodrugs ALL00179 and ALL00180

As can be seen in the table above, high cumulative permeation and flux values were achieved using a water soluble form of CBD (ALL00179). Likewise, short lag times were observed throughout the study for the ALL00179-treated skin. Previous studies showed that ALL00179 and CBD permeation through intact skin (non-MN treated, 100% ddH$_2$O donor solution) gave no flux and drug was detected in the skin in very small amounts (0.09±0.03 μmol/g skin CBD equivalents for ALL00179 and none for CBD). In this study, the total amount of CBD delivered from a 25 mg ALL00179-containing donor solution was 0.2±0.1 mg total CBD equivalents in the skin and 1.0±0.2 mg total CBD equivalents in the receiver solution after 48 hr. This accounts for approximately 4.8% of the total ALL00179 in the donor solution. Analysis of the donor solutions at the end of the study showed 84.3±2.6% ALL00179, 15.7±2.6% ALL00180 and 0% CBD.

As a comparison, permeation from an optimized gel system of cannabidiol (2.5% w/w) through intact dermatomed human skin, dosed every 12 hr, gave a flux of 5.2 nmol/cm$^2$/h. The total CBD flux from ALLL00179 after MN treatment of full thickness Yucatan pig skin was 63.2±11.4 nmol/cm$^2$/h, resulting in a 12.2 fold enhancement of flux.

The use of the terms "a" and "an" and "the" and similar references in the context of this disclosure (especially in the context of the following claims) are to be construed to cover both the singular and the plural, unless otherwise indicated herein or clearly contradicted by context. All methods and individual method steps described herein can be performed in any suitable order or simultaneously unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope, or range of equivalents, to which the appended claims are entitled. No language in the specification should be construed as indicating any non-claimed element as essential to the practice of the present disclosure.

All references, including printed publications, patent applications, and patents, cited herein are hereby incorporated by reference to the same extent as if each reference were individually and specifically indicated to be incorporated by reference and were set forth in its entirety herein.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represents further embodiments of the present disclosure and are included as a part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

We claim:

1. A microneedle drug delivery system for transdermal or topical administration of a cannabidiol prodrug to a mammal comprising:
   (a) a pharmaceutical composition in the form of a hydrogel comprising
      (i) about 0.1% to about 40% of cannabidiol prodrug:

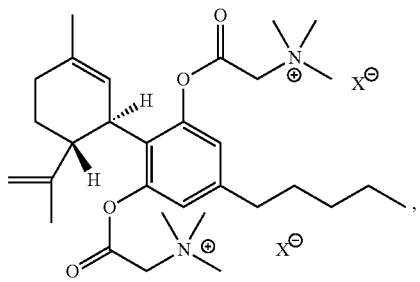

where X⁻ is a counter ion derived from pharmaceutically acceptable acids,
      (ii) about 0.1% to about 20% of one or more co-solvents;
      (iii) about 15% to about 95% a lower alcohol; and
      (iv) water in a quantity sufficient for the composition to total 100% (wt/wt);
   (b) a microneedle array; and
   (c) a matrix- or reservoir-type patch incorporating at least the pharmaceutical composition and the microneedle array.

2. The drug delivery system of claim 1, wherein the cannabidiol prodrug is present in an amount of about 5% to about 30% (wt/wt) of the pharmaceutical composition.

3. The drug delivery system of claim 1, wherein the cannabidiol prodrug is present in an amount of about 10% to about 20% (wt/wt) of the pharmaceutical composition.

4. The drug delivery system of claim 1, wherein each of the one or more co-solvents is selected from the group consisting of: ethanol, benzyl alcohol, and mixtures of the foregoing.

5. The drug delivery system of claim 1, wherein the pharmaceutical composition further comprises a COX inhibitor selected from the group consisting of: a non-specific COX inhibitor, a COX-1 inhibitor and a COX-2 inhibitor.

6. The drug delivery system claim 5, wherein the non-specific COX inhibitor comprises at least one of: aspirin, diclofenac, diflunisal, fenoprofen, flurbiprofen, ibuprofen, indomethacin, ketoprofen, ketorolac, mefenamic acid, meloxicam, nabumetone, naproxen, olsalzine, oxaprozin, piroxicam, salsalate, sulfasalazine, sulindac and tolmetin.

7. The drug delivery system of claim 5, wherein the COX-1 inhibitor comprises at least one of: mofezolac, SC-560 and FR 122047.

8. The drug delivery system of claim 5, wherein the COX-2 inhibitor comprises at least one of: etodolac, celecoxib, rofecoxib, valdecoxib, parecoxib, lumiracoxib and etoricoxib.

9. The drug delivery system of claim 1, wherein the pharmaceutical composition further comprises an antioxidant, wherein the antioxidant comprises at least one of citric acid, butylated hydroxytoluene, ascorbic acid, glutathione, retinol, α-tocopherol, β-carotene, α-carotene, ubiquinone, butylated hydroxyanisole, ethylenediaminetetraacetic acid, selenium, zinc, lignan, uric acid, lipoic acid, and N-acetylcysteine.

10. The drug delivery system of claim 1, wherein the pharmaceutical composition further comprises a penetration enhancer, wherein the penetration enhancer comprises at least one of: isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, acetoacetic ester, N-alkylpyrrolidone, terpenes, n-octanol, sodium oleate, D-limonene, monoolein, cineol, oleyl oleate, ethanol, propanol, butanol, 2-butanol, pentanol, 2-pentanol, hexanol, octanol, nonanol, decanol, benzyl alcohol, Polyxamer 231, Polyxamer 182, Polyxamer 184, Polysorbate 20, Polysorbate 60, Brij 30, Brij 93, Brij 96, Brij 99, Span 20, Span 40, Span 60, Span 80, Span 85, Tween 20, Tween 40, Tween 60, Tween 80, Myrj 45, Myrj 51, Myrj 52, and Miglyol 840.

11. The drug delivery system of claim 10, wherein the penetration enhancer is present in an amount of about 0.1% to about 40% (wt/wt) of the pharmaceutical composition.

12. The drug delivery system of claim 10, wherein the penetration enhancer is present in an amount of about 0.1% to about 30% (wt/wt) of the pharmaceutical composition.

13. The drug delivery system of claim 10, wherein the penetration enhancer is present in an amount of about 1% to about 20% (wt/wt) of the pharmaceutical composition.

14. The drug delivery system of claim 10, wherein the penetration enhancer is present in an amount of about 1% to about 10% (wt/wt) of the pharmaceutical composition.

15. The drug delivery system of claim 1, wherein the lower alcohol comprises at least one of ethanol and isopropanol.

16. The drug delivery system of claim 1, wherein the pharmaceutical composition delivers a therapeutically effective amount of the cannabidiol prodrug over a period of time selected from the group consisting of: about 1 hour, about 2 hours, about 3 hours, about 4 hours, about 6 hours, about 12 hours, about 24 hours, about 48 hours, about 72 hours, about 96 hours, about 5 days, about 6 days or about 7 days.

* * * * *